(12) United States Patent
Hancock et al.

(10) Patent No.: US 11,950,843 B2
(45) Date of Patent: *Apr. 9, 2024

(54) ELECTROSURGICAL APPARATUS

(71) Applicant: Creo Medical Limited, Chepstow Monmouthshire (GB)

(72) Inventors: Christopher Paul Hancock, Bath (GB); George Christian Ullrich, Bangor Gwynedd (GB); David Edward Webb, Gwynedd (GB); Louis Turner, Chepstow (GB); Simon Meadowcroft, Chepstow (GB); Jessi Johnson, Sunnyvale, CA (US); Miriam Taimisto, San Jose, CA (US)

(73) Assignee: CREO MEDICAL LIMITED, Chepstow (GB)

( * ) Notice: Subject to any disclaimer, the term of this patent is extended or adjusted under 35 U.S.C. 154(b) by 180 days.

This patent is subject to a terminal disclaimer.

(21) Appl. No.: 16/643,482

(22) PCT Filed: Oct. 12, 2018

(86) PCT No.: PCT/EP2018/077879
§ 371 (c)(1),
(2) Date: Feb. 28, 2020

(87) PCT Pub. No.: WO2019/073036
PCT Pub. Date: Apr. 18, 2019

(65) Prior Publication Data
US 2020/0253664 A1 Aug. 13, 2020

(30) Foreign Application Priority Data
Oct. 13, 2017 (GB) ...................................... 1716778

(51) Int. Cl.
*A61B 18/00* (2006.01)
*A61B 18/18* (2006.01)

(52) U.S. Cl.
CPC ...................... *A61B 18/1815* (2013.01); *A61B 2018/00202* (2013.01); *A61B 2018/00601* (2013.01);
(Continued)

(58) Field of Classification Search
CPC ...... A61B 18/1815; A61B 2018/00202; A61B 2018/00601; A61B 2018/00607;
(Continued)

(56) References Cited

U.S. PATENT DOCUMENTS 5,545,200 A * 8/1996 West ................. A61M 25/0136
606/29
5,928,228 A * 7/1999 Kordis ................. A61B 5/6858
606/41

(Continued)

FOREIGN PATENT DOCUMENTS

CN 101374465 A 2/2009
EP 3230863 A1 10/2017
(Continued)

OTHER PUBLICATIONS

International Search Report and Written Opinion, issued by International Searching Authority in corresponding International Application No. PCT/EP2018/077879, dated Feb. 5, 2019.

*Primary Examiner* — Joseph A Stoklosa
*Assistant Examiner* — Annie L Shoulders
(74) *Attorney, Agent, or Firm* — ArentFox Schiff LLP

(57) ABSTRACT

An electrosurgical apparatus comprising an electrosurgical forceps instrument that combines la robust jaw opening mechanism with an a microwave energy delivery mechanism. The instrument includes a rigid bracket mounted at a distal end of a flexible shaft, wherein a pair of jaws are (Continued)

pivotably mounted on the rigid bracket. The instrument includes an energy delivery structure comprising a flexible dielectric substrate having a first electrode and an second electrode formed on one of the pair of jaws, wherein the first electrode and the second electrode are arranged to emit microwave energy. The electrosurgical apparatus may also comprise a handpiece that combines rotation control of an electrosurgical instrument with both power delivery and end effector actuation (e.g. jaw closure, blade retraction or the like).

22 Claims, 16 Drawing Sheets

(52) U.S. Cl.
CPC ............... *A61B 2018/00607* (2013.01); *A61B 2018/0063* (2013.01); *A61B 2018/00946* (2013.01); *A61B 2018/00952* (2013.01); *A61B 2018/1823* (2013.01)

(58) Field of Classification Search
CPC ........... A61B 2018/00946; A61B 2018/00952; A61B 2018/1813

See application file for complete search history.

(56) References Cited

U.S. PATENT DOCUMENTS

| | | | |
|---|---|---|---|
| 8,808,345 B2* | 8/2014 | Clark | A61B 34/74 607/113 |
| 9,381,066 B2* | 7/2016 | Hancock | A61B 18/1815 |
| 11,253,313 B2* | 2/2022 | Hancock | A61B 18/1815 |
| 2003/0130711 A1* | 7/2003 | Pearson | A61B 18/1477 607/101 |
| 2013/0046337 A1 | 2/2013 | Evans et al. | |
| 2014/0276738 A1 | 9/2014 | Price et al. | |
| 2014/0358140 A1* | 12/2014 | Emmons | A61N 7/022 606/33 |
| 2015/0012021 A1* | 1/2015 | Mihara | A61B 17/29 606/167 |
| 2016/0278801 A1* | 9/2016 | Michelini | A61B 17/22031 |
| 2017/0215941 A1 | 8/2017 | Kazuno | |
| 2017/0238991 A1 | 8/2017 | Worrell et al. | |
| 2017/0319265 A1* | 11/2017 | Yates | A61B 17/320092 |
| 2018/0171553 A1* | 6/2018 | Rossetti | D03D 11/00 |
| 2018/0256180 A1* | 9/2018 | Tah | A61B 1/00133 |

FOREIGN PATENT DOCUMENTS

| | | |
|---|---|---|
| GB | 2552925 A | 2/2018 |
| RU | 2499574 C2 | 11/2013 |
| WO | WO 00/42926 A1 | 7/2000 |

* cited by examiner

ELECTROSURGICAL APPARATUS

CROSS-REFERENCE TO RELATED APPLICATIONS

This application is a National Stage entry of International Application No. PCT/EP2018/077879, filed on Oct. 12, 2018, which claims priority to British Patent Application No. 1716778.4, filed on Oct. 13, 2017. The disclosures of the priority applications are hereby incorporated in their entirety by reference.

FIELD OF THE INVENTION

The invention relates to electrosurgical forceps for grasping biological tissue and for delivering microwave energy into the grasped tissue to coagulate or cauterise or seal the tissue. In particular, the forceps may be used to apply pressure to close one or more blood vessels before applying electromagnetic radiation (preferably microwave energy) to seal the blood vessel(s). The forceps may also be arranged to cut tissue after coagulate or sealing, e.g. using radiofrequency (RF) energy or a mechanical cutting element, such as a blade. The invention may be applied to forceps that can be inserted down the instrument channel of an endoscope, a gastroscope or a bronchoscope, or may be used in laparoscopic surgery or open surgery.

BACKGROUND TO THE INVENTION

Electrosurgical instruments are instruments that are used to deliver radiofrequency and/or microwave frequency energy to biological tissue, for purposes such as cutting biological tissue or coagulating blood. Radiofrequency and/or microwave frequency energy is supplied to the electrosurgical instrument using a transmission line, such as a coaxial cable, waveguide, microstrip line or the like.

In some cases an electrosurgical instrument may include forceps capable of delivering heat energy biological tissue grasped between jaws of the forceps. For example, radiofrequency (RF) energy may be delivered from a bipolar electrode arrangement in the jaws of the forceps. The RF energy may be used to seal vessel by thermal denaturation of extracellular matrix proteins (e.g. collagen) within the vessel wall. The heat energy may also cauterise the grasped tissue and facilitate coagulation. Alternatively, the jaws may include one or more microwave emitter structures, which are arranged to radiate microwave EM energy into biological tissue grasped between the jaws, in order to seal the tissue. Such devices typically find application on the end of minimal invasive surgical laparoscopic tools but can equally find use in other clinical procedural areas such as gynaecology, endourology, gastrointestinal surgery, ENT procedures, etc. Depending on the context of use, these devices can have differing physical construction, size, scale and complexity.

Current examples of minimally invasive devices that are capable of dissecting body tissue at the same time as achieving haemostasis include the LigaSure vessel sealing technology manufactured by Covidien, and the Thunderbeat platform from Olympus. The LigaSure system is a bipolar forceps arrangement in which current is delivered to seal tissue while pressure is applied. The Thunderbeat platform simultaneously delivers thermal energy generated using an ultrasonic source, and bipolar electrical energy.

U.S. Pat. No. 6,585,735 describes an endoscopic bipolar forceps in which the jaws of the forceps are arranged to conduct bipolar energy through the tissue held therebetween.

EP 2 233 098 describes microwave forceps for sealing tissue in which the sealing surfaces of the jaws include one or more microwave antennas for radiating microwave energy into tissue grasped between the jaws of the forceps.

WO 2015/097472 describes electrosurgical forceps in which one or more pairs of non-resonant unbalanced lossy transmission line structure are arranged on the inner surface of a pair of jaws.

SUMMARY OF THE INVENTION

At its most general, the present disclosure provides various improvements for control of an electrosurgical apparatus, and in particular an electrosurgical forceps instrument. In one aspect, the present disclosure provides an electrosurgical forceps instrument that combines a robust jaw opening mechanism with an microwave energy delivery mechanism. In another aspect, the present disclosure provides a handpiece that combines rotation control of an electrosurgical instrument with both power delivery and end effector actuation (e.g. jaw closure, blade retraction or the like).

According to a first aspect of the invention, there is provided an electrosurgical forceps instrument comprising: a flexible shaft defining a lumen; a coaxial cable for conveying microwave energy disposed within the lumen of the flexible shaft; a rigid bracket mounted at a distal end of the flexible shaft; a pair of jaws pivotably mounted on the rigid bracket, the pair of jaws being movable relative to each other to open and close a gap between opposing inner surfaces thereof; and an actuating element disposed within the lumen of the flexible shaft and extending therefrom through the rigid bracket to operably engage the pair of jaws, wherein the pair of jaws comprises a first jaw having an energy delivery structure attached to an inner surface therefore, the energy delivery structure comprising a flexible dielectric substrate having a first electrode and an second electrode formed thereon, wherein the energy delivery structure is connected to receive the microwave energy from the coaxial cable, and wherein the first electrode and the second electrode are arranged to emit the microwave energy received by the energy delivery structure into the gap between the pair of jaws. This structure can provide a robust jaw opening mechanism, where the pair of jaws are securely mounted with respect to a distal portion of the shaft in a manner that reduces or eliminates the risk of them being deflected e.g. to one side during use. The jaws themselves may be formed as rigid claw-like structures, e.g. from biocompatible metal, such as stainless steel. The jaws may act to protect the energy delivery structure, and thus allow that structure to possess a flexibility that enables it to deform as the jaws move relative to each other without affecting the delivery of microwave power.

In use, the pair of jaws may be arranged to grip biological tissue, e.g. a blood vessel, and apply microwave energy across the gap between the inner surface of the jaws to coagulate the tissue contained within the vessel, i.e. collagen, elastin, fat or blood or a combination of in the biological tissue and therefore seal the gripped vessel. After sealing, the vessel may be cut, e.g. using a blade or RF energy delivered from the same electrodes that deliver the microwave energy. A movable blade may be incorporated into the forceps.

Although the electrodes may be provided on only one of the jaws, it is desirable for them to be provide on both jaws, so that the coagulating effect of the microwave energy is applied in an even manner, which should create a better seal. Thus, the pair of jaws may comprise a second jaw disposed opposite the first jaw, the second jaw having an identical structure to the first jaw. Thus, the pair of jaws may comprise a second jaw having an energy delivery structure attached to an inner surface therefore, the energy delivery structure comprising a flexible dielectric substrate having a first electrode and an second electrode formed thereon, wherein the energy delivery structure is connected to receive the microwave energy from the coaxial cable, and wherein the first electrode and the second electrode are arranged to emit the microwave energy received by the energy delivery structure into the gap between the pair of jaws. In other examples, both jaws may have a flexible dielectric substrate, each with a single electrode. The microwave energy may then be delivered by a transmission line structure formed from the electrodes on both jaws.

The rigid bracket may be a pronged or U-shaped structure mounted at e.g. affixed to the distal end of the flexible shaft. An axle or pivot pin may be mounted between the prongs or legs of the U-shaped structure. The pair of jaws may be pivotably mounted about this same axis, i.e. they may pivot about a common axis.

The pair of jaws may move in a symmetrical manner with respect to the axis. In one example, the pair of jaws may comprise a first jaw and a second jaw, and the actuating element may comprises a first control wire connected to the first jaw and a second control wire connected to the second jaw. The first control wire and second control wire may be movable in a longitudinal direction relative to the bracket to effect opening and closing of the pair of jaws. Each control wire may be secured to, e.g. bonded to or hooked on to, a proximal portion of its respective jaw. The control wires may be rigid to enable both a push force and a pull force to be transferred to the pair of jaws.

The actuating element may comprise a main control wire that extends through the lumen of the flexible shaft. The main control wire may bifurcate at a distal end thereof to form the first control wire and the second control wire.

A retaining frame may be mounted within a proximal portion of the lumen to hold the coaxial cable and the actuating element in a fixed orientation relative to each other. The retaining frame may have a first mounting region shaped to receive and retain the coaxial cable and a second mounting region shaped to receive and retain the actuating element. A sleeve may be formed around the retaining frame, coaxial cable and actuating element within the lumen of the flexible shaft. This arrangement may reduce friction as the flexible shaft is manipulated, and may assist in relative sliding between the actuating element and coaxial cable.

The retaining frame may have a distal end spaced longitudinally from the rigid bracket. In this arrangement a distal portion of the flexible shaft adjacent to the rigid bracket has an emptier lumen and can therefore exhibit more flexibility. This may facilitate locating the instrument in awkward positions.

The first and second electrodes may be elongate conductive elements formed on the flexible dielectric substrate within the jaw. They may be parallel transmission lines, and may form a co-planar line structure on the inner surface. The distance of separation between the co-planar lines or parallel transmission lines may be chosen to provide RF cutting functionality, i.e. to enable an E-field produced upon applying RF energy to be high enough to produce tissue cutting or dissection/resection. The parallel transmission electrodes may be arranged such that the electrodes that opposed each other across the gap between the jaws are of opposite polarity, i.e. a positive charge on one line faces a negative charge of the opposing line. The tissue cutting action may be augmented by the opposing E-fields on the two opposite faces when the jaws are in close proximity, e.g. equal to or less than 1 mm apart, preferably equal to or less than 0.5 mm apart. The spacing between the first and second electrodes on the jaw may be equal to or less than 0.5 mm.

The flexible dielectric substrate may comprise a proximal portion extending between a distal end of the coaxial cable and a proximal end of the inner surface, wherein the proximal portion is deformable upon opening and closing of the pair of jaws. The proximal portion may pass through the rigid bracket. The coaxial cable may thus terminate within the lumen of the flexible shaft.

The flexible dielectric substrate has a pair of conductive tracks formed thereon for conveying microwave energy from the coaxial cable to the first electrode and second electrode. The pair of conductive tracks may be formed on opposite sides of the flexible dielectric substrate. For example, the pair of conductive tracks may comprise a first conductive track electrically connected to an inner conductor of the coaxial cable, and a second conductive track electrically connected to an outer conductor of the coaxial cable.

The first conductive track may be electrically connected to the first electrode and the second conductive track is electrically connected to the second electrode. These connections may occur at a junction at the inner surface of the jaw.

The flexible dielectric substrate may be a ribbon of insulating material having electrically conductive material fabricated thereon to provide the first electrode and the second electrode. The ribbon may have a width greater than a width of the pair of conductive tracks. There may be an additional piece of dielectric (e.g. ceramic or PTFE or ceramic loaded PTFE) mounted on the inner jaw element. In order to minimise power loss in the flexible dielectric substrate and to ensure the material can withstand voltages associated with RF cutting, i.e. peak voltages of up to 400 V or more, the material preferably has a low dissipation factor or tan delta, i.e. 0.001 or lower, and has a high dielectric strength or breakdown voltage, i.e. up to 100 kV/mm or more. Polyimide or similar materials can be used.

The first jaw (or both or the pair of jaws) may have a longitudinal slot formed therein for permitting passage of a cutting blade. The cutting blade may be slidably mounted on the first jaw. The blade may be operable using a blade control wire that is disposed within and extends from the lumen to operably engage the blade. The first jaw comprises a cover portion, e.g. at a distal end thereof. The cover portion may be sized to retain the blade in a retracted position. The blade may be biased into the retracted position. Alternatively or additionally, the blade control wire may be operably coupled to the actuating element such that movement of the blade away from the retracted position urges the pair of jaws towards a closed position. These features may be used separately or in combination to prevent accidental exposure of the blade.

The pair of jaws may be dimensioned to fit within an instrument channel of a surgical scoping device, e.g. an endoscope, gastroscope, bronchoscope or the like.

In another aspect, the invention may provide a handpiece for controlling an electrosurgical instrument, the handpiece comprising: a body; a flexible shaft extending from a proximal end of the body; a coaxial cable extend through a lumen defined by the flexible shaft, the coaxial cable being for connection to an electrosurgical instrument locatable at a distal end of the flexible shaft; a control rod extending through the lumen, the control rod being for connection to an electrosurgical instrument locatable at a distal end of the flexible shaft; an actuating element slidably mounted on the body; and a rotator rotatably mounted on the body, wherein the coaxial cable and the flexible shaft are mounted to slide relative to the body with the actuating element and rotate relative to the body with the rotator, and wherein the control rod has a proximal portion that is mounted in a longitudinally fixed position relative to the body. In use, the handpiece can deliver power to an electrosurgical instrument at the distal end of the flexible shaft in combination with both a longitudinal (axial) force (via the control rod) and rotational force (via the flexible shaft). The longitudinal force may be used to control an end effector on the instrument, e.g. a pair of jaws in a forceps instrument as discussed above, or a sliding blade or needle. The rotational force may be used to control the orientation of the instrument.

The connection between the components in the handpiece are such that the flexible shaft and the coaxial cable are slidably relative to the control rod. In other words, the position of the control rod can change relative to the flexible shaft, which can thus provide a physical movement at the distal end thereof for operating the instrument.

The body may be a barrel-type housing that lies on a axis that is aligned with the flexible shaft as it extends away from the body. A rotation axis of the rotator may be aligned with or coaxial within the axis of the body. The rotator may be a collar or ring mounted on an outer surface of the body. The rotator may be retained in a longitudinal (axial) direction on the body. For example, the body may have a circumferential recess in which the rotator is seated.

The control rod may be rotatable with respect to the body. This means that all of flexible shaft, control rod and coaxial cable rotate relative to the body upon rotation of the rotator. This can prevent twisting of components within the flexible shaft. In one example, the proximal portion of the control rod may be mounted on the rotator. If the rotator is axially fixed relative to the body, this attachment means that the control rod will rotate with the rotator but will not slide relative to the body. The proximal portion may include a radial extension that passes through the flexible shaft in order to connect to the rotator.

The handpiece may comprise an internal shaft that housing a proximal portion of the flexible shaft. The internal shaft may be coupled to the rotator to rotate with it. The internal shaft may be axially slidably along a track formed within the rotator.

The actuating element may comprise a shaft mounted to slide in a longitudinal direction (i.e. the axial direction mentioned above) within the housing. The actuating element and body may have grip elements, e.g. finger rings or the like, for a user to hold while operating the device.

The handpiece may comprise a power input port on the actuating element. The power input port may be a QMA connector or the like. The power input port may be connected to transfer power received therein to the coaxial cable. Thus, a proximal end of the coaxial cable may be connected to the actuating element to receive power from the power input port. The proximal end of the coaxial cable may be connected to the actuating element via a rotatable coupling to permit relative rotation therebetween.

The power input port may connect to an external coaxial cable e.g. from an electrosurgical generator. A connection direction into the power input port may extend perpendicularly to the direction in which the actuating element is slidable relative to the body. For example, the power input port may be at an underside of the actuating element.

In another aspect of the invention, a filter for blocking unwanted frequencies of energy may be incorporated into the handpiece. The filter may be located in the actuating element, so that it moves with the coaxial cable. In one example, the filter is an RF blocking circuit mounted in the actuator element between the power input port and the coaxial cable. If the electrosurgical generator is capable of delivery both RF and microwave energy, but the electrosurgical instrument is designed only to use microwave energy, the RF blocking circuit provides a safety mechanism to prevent incorrect use. This aspect of the invention may share any one or more of the features discussed above.

The handpiece discussed above may be used in an electrosurgical apparatus comprising an electrosurgical generator for supplying microwave energy and a surgical scoping device having an instrument cord for insertion into a patient's body, the instrument cord having an instrument channel extending therethrough. The handpiece may be connected to receive the microwave energy from the electrosurgical generator. The flexible shaft of the handpiece may pass through the instrument channel of the surgical scoping device. An electrosurgical forceps instrument, e.g. such as that discussed herein, may be connected at a distal end of the flexible shaft of the handpiece. The actuating element of the handpiece (which is also the actuating element of the instrument) is connected to control opening and closing of the electrosurgical forceps instrument. The rotator operates to control rotation of the electrosurgical forceps instrument relative to the instrument channel.

The term "surgical scoping device" may be used herein to mean any surgical device provided with an insertion tube that is a rigid or flexible (e.g. steerable) conduit that is introduced into a patient's body during an invasive procedure. The insertion tube may include the instrument channel and an optical channel (e.g. for transmitting light to illuminate and/or capture images of a treatment site at the distal end of the insertion tube. The instrument channel may have a diameter suitable for receiving invasive surgical tools. The diameter of the instrument channel may be 5 mm or less.

Herein, the term "inner" means radially closer to the centre (e.g. axis) of the instrument channel and/or coaxial cable. The term "outer" means radially further from the centre (axis) of the instrument channel and/or coaxial cable.

The term "conductive" is used herein to mean electrically conductive, unless the context dictates otherwise.

Herein, the terms "proximal" and "distal" refer to the ends of the elongate probe. In use the proximal end is closer to a generator for providing the RF and/or microwave energy, whereas the distal end is further from the generator.

In this specification "microwave" may be used broadly to indicate a frequency range of 400 MHz to 100 GHz, but preferably the range 1 GHz to 60 GHz. Specific frequencies that have been considered are: 915 MHz, 2.45 GHz, 3.3 GHz, 5.8 GHz, 10 GHz, 14.5 GHz and 24 GHz. In contrast, this specification uses "radiofrequency" or "RF" to indicate a frequency range that is at least three orders of magnitude lower, e.g. up to 300 MHz, preferably 10 kHz to 1 MHz, and most preferably 400 kHz.

BRIEF DESCRIPTION OF THE DRAWINGS

Embodiments of the present invention will now be discussed, by way of example only, with reference to the accompanying Figures, in which:

FIGS. 7b and 7c are perspective views of the circuit board of FIG. 7a;

DETAILED DESCRIPTION; FURTHER OPTIONS AND PREFERENCES

Figure 1:
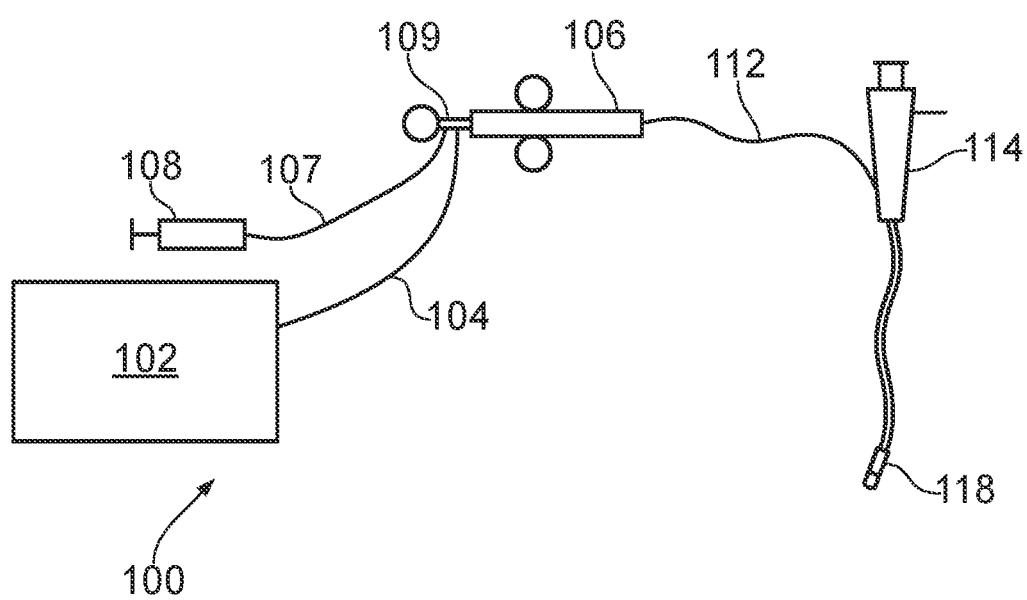
FIG. 1 is a schematic diagram of an electrosurgical system that is an embodiment of the invention.

FIG. 1 is a schematic diagram of a complete electrosurgical system 100 that is an embodiment of the invention. The system is arranged to treat biological tissue (e.g. a tumour, lesion or fibroid) using microwave frequency energy from an instrument tip. The system 100 comprises a generator 102 for controllably supplying microwave EM energy. In some cases the generator 102 may also be capable of supplying RF electromagnetic (EM) energy. A suitable generator for this purpose is described in WO 2012/076844, which is incorporated herein by reference. The generator 102 is connected to a handpiece 106 by an interface cable 104. The handpiece 106 may also be connected to receive a fluid supply 107 from a fluid delivery device 108, such as a syringe, although this is not essential. If needed, the handpiece 106 may house an instrument actuation mechanism that is operable by an actuator 109, e.g. a thumb operated slider or plunger. For example the instrument actuation mechanism may be used to operate the jaws of a forceps instrument as discussed herein. Other mechanisms may also be included in the handpiece. For example, a blade and/or needle movement mechanism may be provided (operable by a suitable trigger on the handpiece) for moving a cutting blade or deploying a needle at the instrument. A function of the handpiece 106 is to combine the inputs from the generator 102, fluid delivery device 108 and instrument actuation mechanism, together with any other inputs which may be required, into a single flexible shaft 112, which extends from the distal end of the handpiece 106.

The flexible shaft 112 is insertable through the entire length of an instrument (working) channel of a surgical scoping device 114. The flexible shaft 112 has an instrument tip 118 that is shaped to pass through the instrument channel of the surgical scoping device 114 and protrude (e.g. inside the patient) at the distal end of the endoscope's tube. The instrument tip 118 includes a pair of jaws for gripping biological tissue and an energy delivery structure arranged to emit microwave EM energy which is conveyed from the generator 102. Optionally the instrument tip 118 may also include a movable blade for cutting biological tissue, and/or a retractable hypodermic needle for delivering fluid conveyed from the fluid delivery device 108. As described in more detail below, the handpiece 106 includes an actuation mechanism for opening and closing the jaws of the instrument tip 118. The handpiece 106 also includes a rotation mechanism for rotating the instrument tip 118 relative to the instrument channel of the surgical scoping device 114.

The structure of the instrument tip 118 may be arranged to have a maximum outer diameter suitable for passing through the working channel. Typically, the diameter of a working channel in a surgical scoping device such as an endoscope is less than 4.0 mm, e.g. any one of 2.8 mm, 3.2 mm, 3.7 mm, 3.8 mm. The length of the flexible shaft 112 can be equal to or greater than 1.2 m, e.g. 2 m or more. In other examples, the instrument tip 118 may be mounted at the distal end of the flexible shaft 112 after the shaft has been inserted through the working channel (and before the instrument cord is introduced into the patient). Alternatively, the flexible shaft 112 can be inserted into the working channel from the distal end before making its proximal connections. In these arrangements, the distal end assembly 118 can be permitted to have dimensions greater than the working channel of the surgical scoping device 114. The system described above is one way of introducing the instrument into a patient. Other techniques are possible. For example, the instrument may also be inserted using a catheter.

Instrument Tip Structure

Figure 2A:
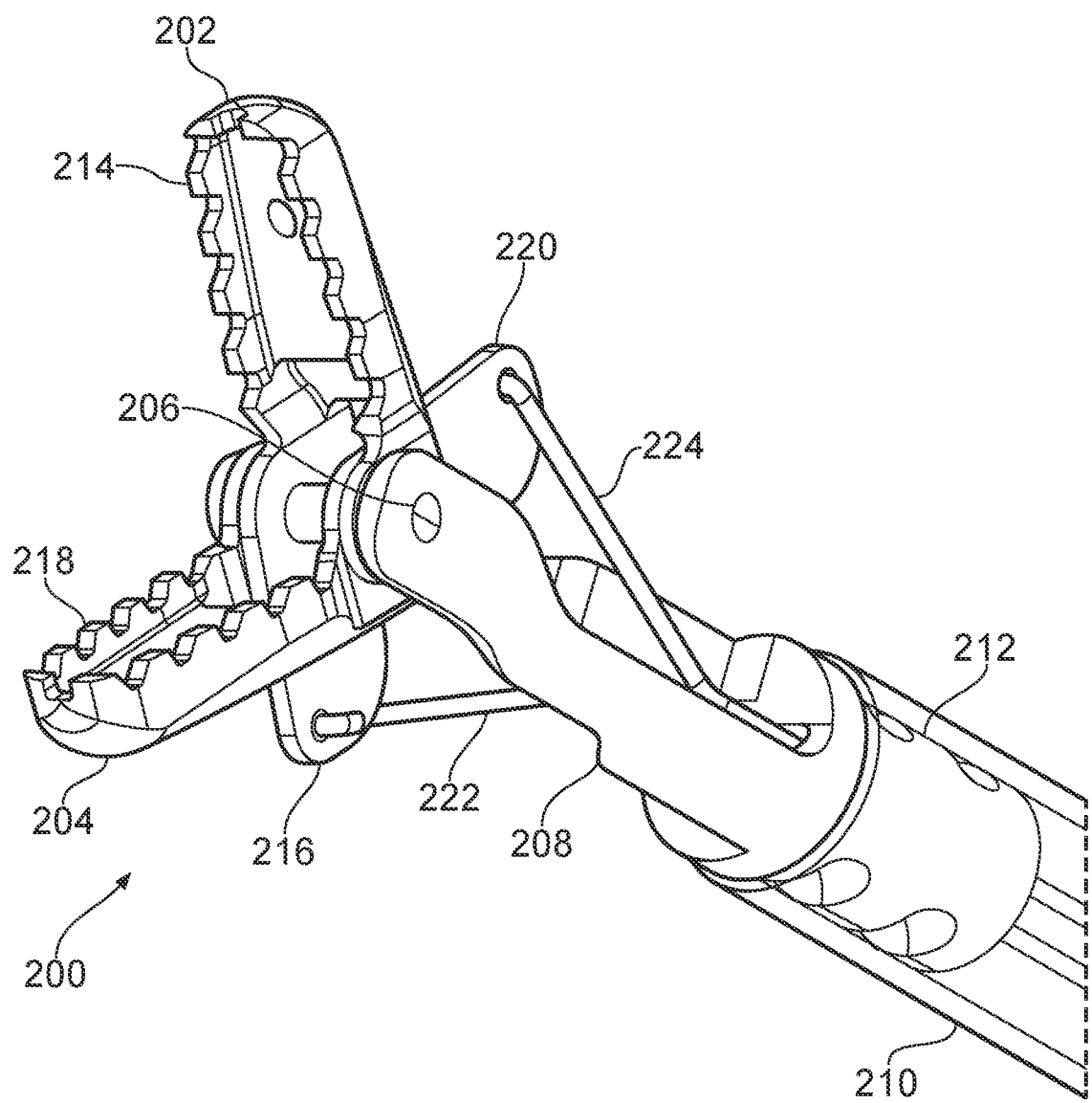
FIGS. 2a, 2b and 2c show perspective views of an instrument tip of an electrosurgical forceps instrument that is an embodiment the invention.

FIG. 2a is a schematic diagram showing a perspective view of an instrument tip 200 of an electrosurgical forceps instrument that is an embodiment of the invention. The instrument tip 200 includes a first jaw 202 and a second jaw 204, each of which is pivotally mounted on an axle 206 such that they are movable relative to each other to open and close a gap between them. The jaws may be made of metal, e.g. stainless steel or other biocompatible material. The axle 206 is mounted on a rigid bracket 208 which protrudes from a distal end of an instrument shaft 210. The bracket 208 includes a mounting portion 212 which is shaped to extend into and close a distal end of the instrument shaft 210. The bracket 208 may be secured to the instrument shaft 210 with an adhesive or some other suitable means (e.g. ultrasonic welding). In this manner, any torque applied to the instrument shaft 210 may be transmitted to the instrument tip 200. The instrument shaft 210 may comprises a hollow tube made of any suitable material, e.g. PTFE.

The first jaw 202 includes a gripping portion 214 for gripping biological tissue and an actuation portion 216 for pivoting the jaw 202 about the axle 206. The gripping portion 214 and actuation portion 216 are located on opposing ends of the jaw 202, either side of the axle 206. The gripping portion 214 is located at a distal end of the instrument tip 200, whilst the actuation portion 216 is located closer to the instrument shaft 210. Similarly, second jaw 204 includes a gripping portion 218 and an actuation portion 220 located on either side of the axle 206. The gripping portions 214 and 218 may each include serrated edges, to facilitate the gripping of biological tissue. The jaws 202 and 204 are pivotally mounted on the axle 206 such that a gap between the gripping portions 214 and 218 of the jaws can be varied (i.e. the gap can be opened and closed). In use, this enables biological tissue to be gripped between the gripping portions 214, 218 of the jaws 202, 204.

A first control wire 222 is connected to the actuation portion 216 of the first jaw 202, and a second control wire 224 is connected to the actuation portion 220 of the second jaw 204. The first and second control wires 222, 224 pass through the bracket 208 into the instrument shaft 210, and run along the entire length of the instrument shaft 210. The first and second control wires 222, 224 are connected at a proximal end of the electrosurgical instrument to a handpiece (discussed in more detail below), which can be used to move the control wires forwards and backwards along the instrument shaft 210. The control wires 222, 224 may pass through the bracket 208 via holes in the mounting portion 212 of the bracket 208. In order to prevent fluids from entering into the instrument shaft 210 via the holes in the mounting portion 212, tubes made of a suitable material (e.g. polyimide) which are arranged to form a water-tight seal around the control wires may be placed inside the holes. Such tubes may also serve to prevent glue (e.g. which is used during manufacture to glue the bracket 208 to the instrument shaft 210) from accidentally dripping onto the control wires 222, 224 and causing them to stick.

In the example shown, the gripping portions 216, 220 each include a hole for receiving the first and second control wires 222, 224 respectively. The first and second control wires 222, 224 each include a hook at their distal ends for mechanically engaging the hole in actuation portions 216 and 220 respectively. Other manners of securing the control wires 222, 224 to the gripping portions 216, 220 are also possible.

For example, the control wires may be glued, soldered or welded to the gripping portions.

Longitudinal motion of the first and second control wires 222, 224 along the instrument shaft 210 causes the jaws 202, 204 to pivot about the axle 206, varying the gap between the gripping portions 214, 218 of the jaws. For example, if the first and second control wires 222, 224 are pushed along the instrument shaft 210 (i.e. they are pushed towards the instrument tip 200), the jaws 202, 204 pivot such that their gripping portions 214, 218 move away from each other, thus opening a gap between the gripping portions 214, 218. Conversely, if the first and second control wires 222, 224 are pulled along the instrument shaft 210 (i.e. retracted away from the instrument tip 200), the jaws 202, 204 pivot such that their gripping portions 214, 218 move towards each other, thus closing the gap between them.

The first and second control wires 222, 224 may be moved together along the instrument shaft 210, or they may be moved independently of one another. Moving the control wires together may cause the jaws to move symmetrically relative to a longitudinal axis of the instrument shaft 210. This may facilitate gripping of biological tissue between the jaws. In other examples, one of the jaws may be fixed relative to the bracket 208 (i.e. it does not pivot relative to an axle) and only one of the jaws may be pivotally mounted on an axle. In such an example, there may be only a single control wire which is connected to the pivotally mounted jaw.

Figure 2B:
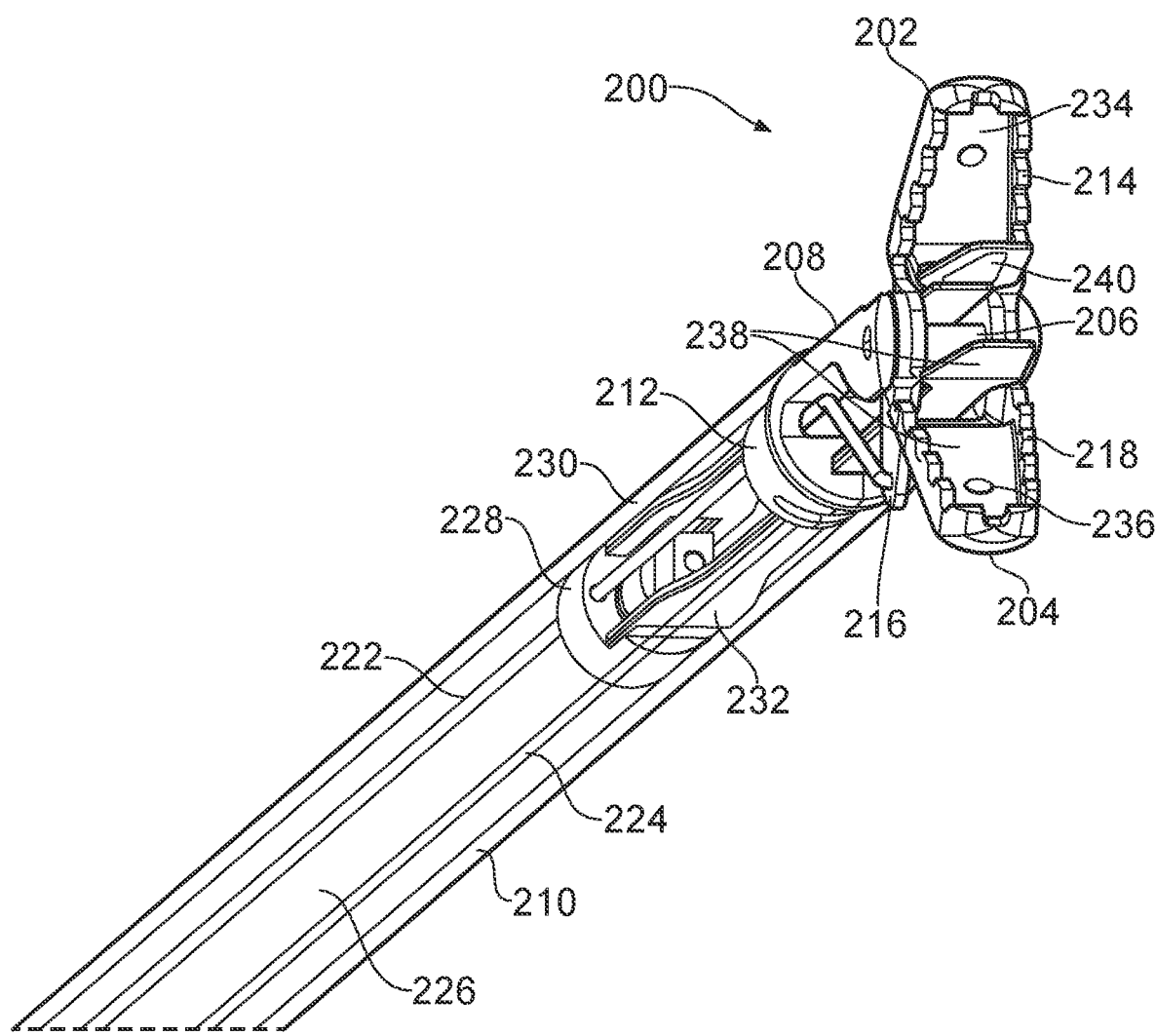

FIG. 2b is a schematic diagram showing a different perspective view of instrument tip 200. Where features have already been described above in reference to FIG. 2a, identical reference numerals have been used.

A coaxial transmission line 226 passes through the instrument shaft 210. The coaxial transmission line 226 is serves to convey radiofrequency (RF) electromagnetic (EM and/or microwave EM energy from a generator (e.g. generator 102) to the instrument tip 200. The coaxial transmission line 226 may be a conventional flexible coaxial cable, and includes an inner conductor separated from an outer conductor by a dielectric material. The coaxial transmission line 226 may also include a protective outer dielectric layer. The coaxial transmission line 226 terminates at a connector 228 located (e.g. secured or otherwise fixed) inside the instrument shaft 210. The first and second control wires 222, 224 run alongside the coaxial transmission line 226 inside the instrument shaft 210, and extend through openings in the connector 228 so that they can be connected to the jaws 202, 204 in the manner described above.

A first flexible microwave substrate 230 and a second flexible microwave substrate 232 are secured to the connector 228, e.g. using an adhesive. In the example shown, the connector 228 includes a pair of longitudinally extending ledges to which the flexible microwave substrates are secured. The flexible microwave substrates 230, 232 (which may also be referred to as electrode strips) may be made of any suitable flexible dielectric material. For example, the flexible microwave substrates 230, 232 might be RFlex microwave substrate from Rogers Corporation.

The first flexible microwave substrate 230 extends from the connector 228 and passes through an aperture in the mounting portion 212 of the bracket 208. A distal portion of the first flexible microwave substrate 230 is secured to an inner surface 234 of the first jaw 202. Similarly, the second flexible microwave substrate 232 extends from the connector 228, passes through an aperture in the mounting portion 212 of the step 208, and is secured at a distal portion to an inner surface 236 of the second jaw 204. Note that for illustration purposes, the first and second flexible microwave substrates 230, 232 are not shown as being secured to the inner surfaces of jaws 202, 204; they are shown in a state before they are secured to the inner surfaces of the jaws 202, 204. The flexible microwave substrates may be secured to the inner surfaces of the jaws 202, 204 using any suitable bonding or fixing method. For example, they may be attached by an adhesive. Alternatively, the flexible microwave substrates may be secured to their respective inner surface using solder. FIG. 2b shows a patch of solder 238 applied to an underside of the second flexible microwave substrate 232. Solder flux (not shown) is applied to the inner surface 236 of the jaw 204. The second flexible microwave substrate 232 may then be bonded to the inner surface 236 by pressing the second flexible microwave substrate 232 onto the inner surface 236 and heating the jaw 204 (e.g. with the tip of a soldering iron), which causes the solder to flow and distribute itself evenly between the second flexible microwave substrate 232 and the inner surface 236. Note that for illustration purposes, flexible microwave substrates 230, 232 are not depicted in FIG. 2a.

A microwave emitter structure is formed on the distal portion of each of the flexible microwave substrates 230, 232. FIG. 2b shows for example microwave emitter structure 240 on the distal portion of flexible microwave substrate 230. Each microwave emitter structure is connected to receive microwave EM energy from the coaxial transmission line via conductive paths on the flexible microwave substrates. Each microwave emitter structure may be configured to emit microwave EM energy into biological tissue gripped between the jaws 202, 204. For example, one or both of the microwave emitter structures may be a coplanar microstrip antenna having an active strip and a ground strip. In such a case, the flexible microwave substrate may include two conductive paths: a first conductive path connecting the inner conductor of the coaxial transmission line 226 to the active strip and a second conductive path connecting the outer conductor of the coaxial transmission line 226 to the ground strip. Other types of microwave emitter structure are also possible.

In some cases, the instrument tip 200 may include a single microwave emitter structure which is split between the two jaws 202, 204. For example, an active strip which is connected to the inner conductor of the coaxial transmission line 226 may be formed on the distal portion of the first flexible microwave substrate 230, whilst a ground strip connected to the outer conductor of the coaxial transmission line 226 may be formed on the distal portion of the second flexible microwave substrate 232. In other examples, the instrument tip 200 may include a single microwave emitter structure formed on a single jaw. In such a case, it may only be necessary to provide a single flexible microwave substrate.

The microwave emitter structure and conductive paths on a flexible microwave substrate may be formed of a conductive material which is deposited on the flexible microwave substrate. For example, the emitter structure and conductive paths may be formed of a metal which is printed onto the flexible microwave substrate. The flexible microwave substrates therefore serve both to provide a support for the microwave emitter structures, and to connect the microwave emitter structures to the coaxial transmission line 226.

As the flexible microwave substrates are flexible, they bend when the jaws 202, 204 are opened and closed, thus allowing movement of the jaws whilst maintaining the connection between the microwave emitter structures and the coaxial transmission line 226. The bending of the flexible microwave substrates 230, 232 may take place mainly near the distal portions of the flexible microwave substrates, which are secured to the jaws 202, 204. This avoids putting large mechanical stresses on the connections between the connector 228 and the flexible microwave substrates 230, 232. This ensures that electrical connection is maintained between the microwave emitter structures and the coaxial transmission cable, even after repeated opening and closing of the jaws 202, 204. Furthermore, the apertures in the mounting portion 212 of the bracket 208 through which the flexible microwave substrates 230, 232 pass may be arranged to restrict movement of the flexible microwave substrates 230, 232 relative to the instrument shaft, in order to reduce mechanical stresses experienced at the connector 228 due to bending of the flexible microwave substrates 230, 232.

The instrument tip 200 may thus be used to seal biological tissue (e.g. a blood vessel) held between the jaws 202, 204, by applying microwave EM energy to the biological tissue with the microwave emitter structure.

Figure 2C:
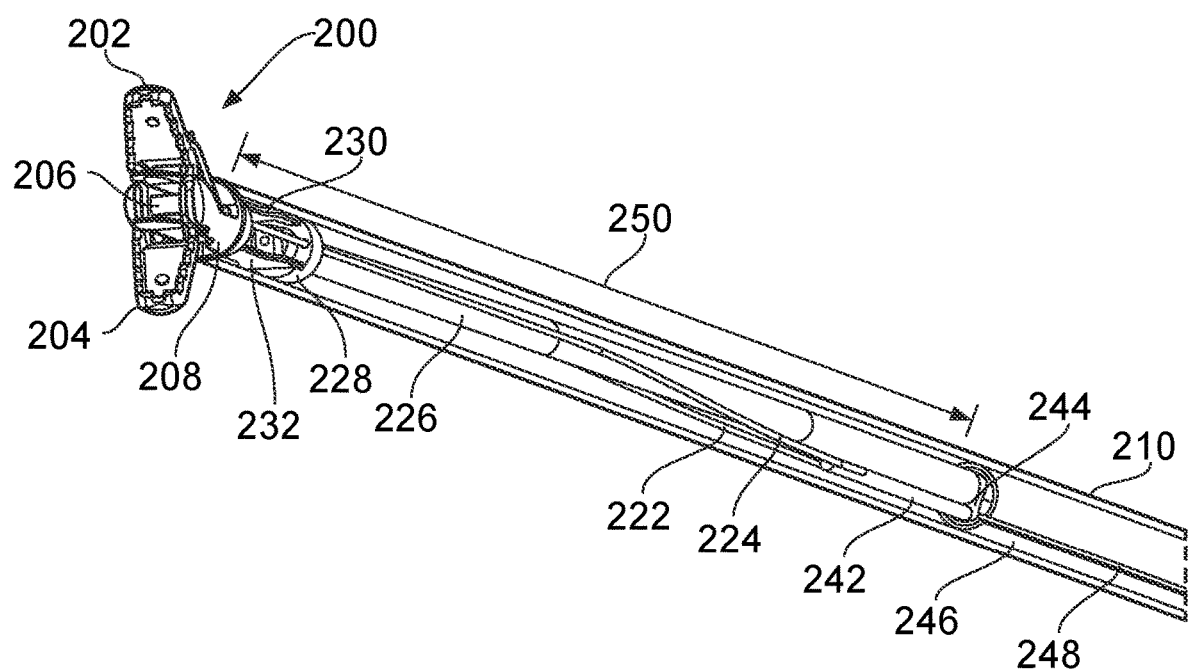

FIG. 2c is a schematic diagram showing a perspective view of instrument tip 200, together with a length of the instrument shaft 210. Where features have already been described above in reference to FIGS. 2a and 2b, identical reference numerals have been used.

As shown in FIG. 2c, the first and second control wires 222, 224 are connected to a single main control wire 242 part way along the instrument shaft 210. The first and second control wires 222, 224 may for example be glued, welded or soldered to the main control wire 242. In this manner, a longitudinal motion of the main control 242 along the instrument shaft 210 may be transmitted to the first and second control wires 222, 224, causing the jaws 202, 204 to move. The main control wire 242 runs along the instrument shaft 210 between the first and second control wires 222, 224 and the handpiece (discussed in more detail below). The first and second control wires 222, 224 are connected to the main control wire 242 near the distal end of the instrument shaft 210, such that only a single control wire (namely the main control wire 242) runs along most of the length of the instrument shaft 210. This may simplify construction of the electrosurgical instrument.

Part way along the instrument shaft 210, the coaxial transmission line 226 and the main control wire 242 enter a wire holder 244 having a first passage in which a portion of the coaxial transmission line 226 is contained and a second passage in which a portion of the main control wire 242 is contained. The wire holder 244 serves to fix the lateral positions of the coaxial transmission line 226 and main control wire 242 relative to one another, whilst allowing the main control wire 242 to move longitudinally along the instrument shaft 210. The wire holder 244 therefore prevents the coaxial transmission line 226 and main control wire 242 from becoming tangled or twisted inside the instrument shaft 210, which could affect the accuracy with which opening and closing of the jaws can be controlled. In cases where other wires (e.g. a blade control wire) or conduits (e.g. a fluid conduit) are used, the wire holder 244 may also include further passages for holding the additional wires and/or conduits. The wire holder may be made out of plastic, for example it may be an extrusion made of polyether ether ketone (PEEK).

The wire holder 244 may itself be contained within a tube 246 (e.g. a PEEK tube). The tube 246 may have a split 248 along its length, to facilitate insertion of the wire holder into the tube 246. The tube 246 may act as padding between the wire holder 244 and an inner surface of the instrument shaft 210, in order to prevent the wire holder 244 from moving inside the instrument shaft 210. This may help avoid lag when pushing or pulling the main control wire 242 to move the jaws 202, 204.

The distal ends of the wire holder 244 and tube 246 are spaced from the instrument tip 200 by a predetermined distance. The instrument shaft 210 therefore includes a distal portion 250 between the instrument tip 200 and the distal ends of the wire holder and tube 246 where there is no wire holder 244 or tube 246. The wire holder 244 and tube 246 may extend along the instrument shaft 210 most or all of the length between their distal ends and the handpiece. The distal portion 250 of the instrument shaft 210 may therefore have increased flexibility compared to the rest of the instrument shaft 210. This may improve the manoeuvrability of the instrument shaft 210, as it may enable the distal portion 250 to be guided through tightly bending passageways. The lack of a wire holder 244 and tube 246 in the distal portion 250 also serves to provide space for the connection between the first and second control wires 222, 224 and the main control wire 242. In some embodiments, the length of the distal portion 250 of the instrument shaft 210 may be 150 mm.

Figure 3A:
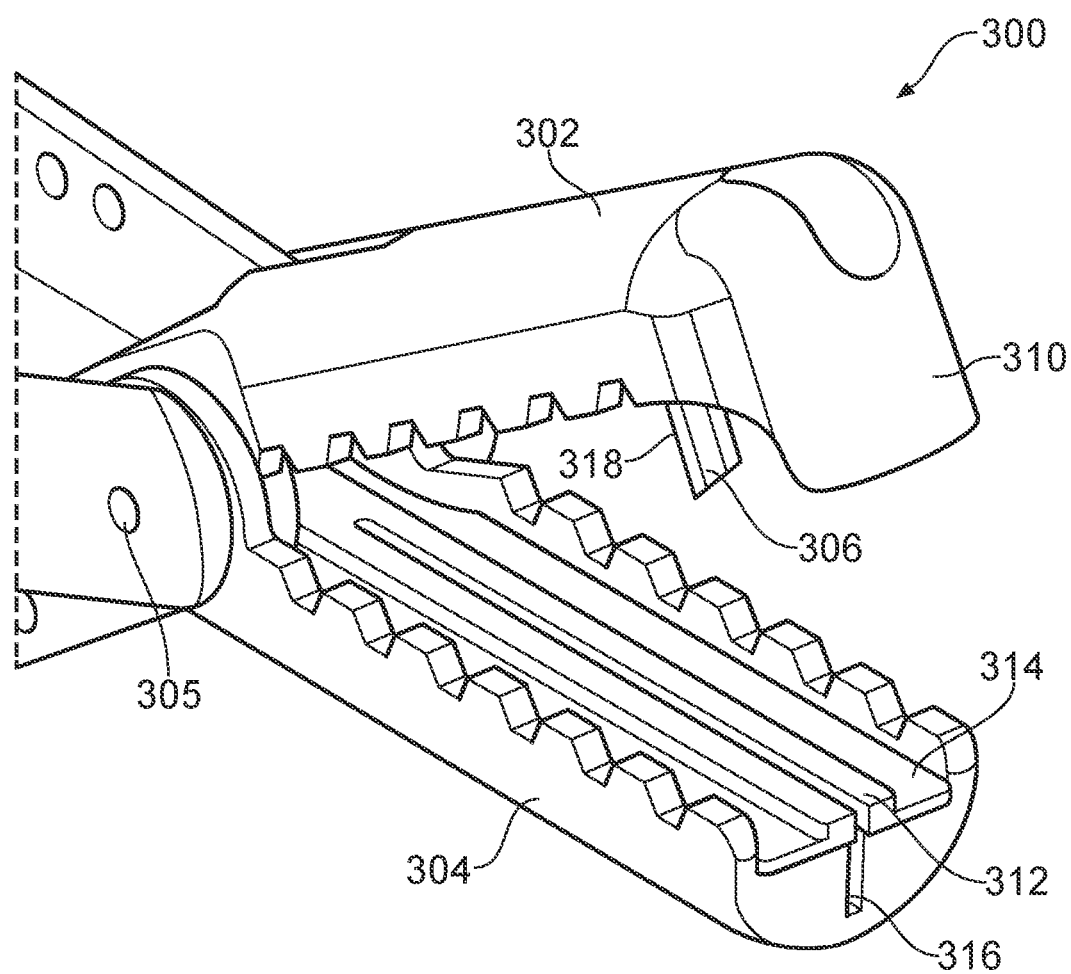
FIGS. 3a, 3b show perspective views of an instrument tip of an electrosurgical forceps instrument that is another embodiment of the invention.
Figure 3B:
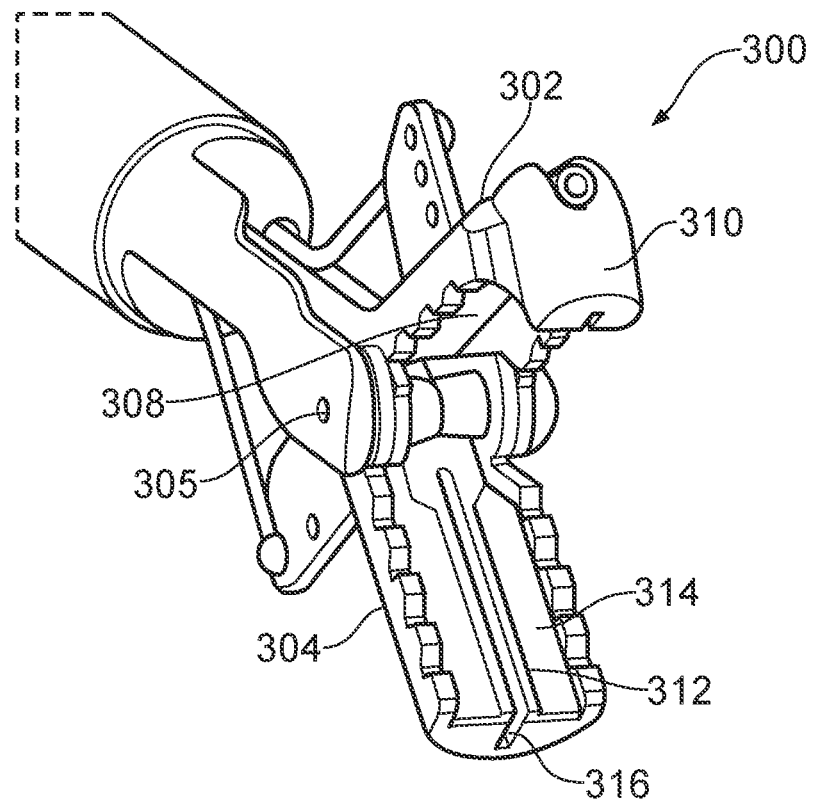

FIGS. 3a and 3b show perspective views of another instrument tip 300 of an electrosurgical instrument according to the invention. The instrument tip 300 includes a first jaw 302 and a second jaw 304 pivotally mounted on an axle 305. The first and second jaws 302, 304 include gripping portions 306, 308 respectively for gripping biological tissue between them. Similarly to instrument tip 200 discussed above, jaws 302, 304 also include actuation portions to which control wires (not shown) are attached, in order to open and close the jaws.

The first jaw 302 includes a blade 306 which is movable along a longitudinally extending slot 308 in the jaw 302. The blade may be moved backwards and forwards along the slot 308 by means of a control wire (not shown) attached to the blade 306 and which runs through the instrument shaft to the handpiece. The first jaw 302 further includes a cover 310 at its distal end, into which the blade 306 can be retracted so that it is not exposed. Thus, when the blade 306 is not in use, it may be retracted into the cover 310 in order to avoid unintentionally cutting any tissue. The blade 306 may be biased towards a retracted position where it is concealed by the cover 310.

Figure 3C:
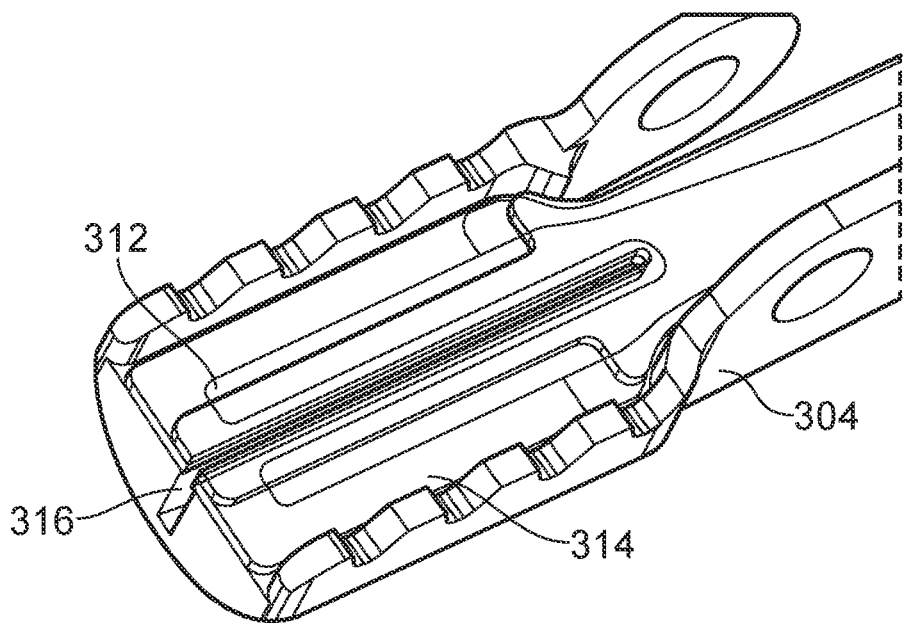
FIG. 3c shows a perspective view of a jaw of the instrument tip of FIGS. 3a and 3b.

The second jaw 304 includes a microwave emitter structure 312 deposited on a flexible microwave substrate 314 in a manner similar to that described above in relation to instrument tip 200. The microwave emitter structure 312 may be arranged to emit microwave EM energy into tissue gripped between the jaws 302, 304. The second jaw 304 further includes a slot 316 for receiving the blade 306. The slot 316 passes through part of the microwave emitter structure 312 and the flexible microwave substrate 314, such that the active electrode 315 is split into two prongs, as illustrated in FIG. 3c which shows a schematic diagram of second jaw 304. The slot 316 on the second jaw 304 is aligned with the slot 308 on the first jaw, such that when the jaws are brought together, the blade 306 may be received in slot 316 of the second jaw 304 and moved backwards and forwards along the slot 316. Both slots 308 and 316 are oriented in the longitudinal direction (i.e. along an axis of the instrument shaft). The blade 306 includes a cutting edge 318 which faces inwards, towards the axle 305. In this manner, biological tissue held between the jaws 302, 304 may be cut by pulling the blade along the slot 308 towards the axle 305. The maximum length of cut which can be achieved with instrument tip 300 is determined by the length of the jaws 302, 304 and of slots 308 and 316, as these determine the range of motion of the blade 306. Longer slots 308, 316 may enable longer cuts to be performed.

An example use of the instrument tip 300 will now be described. First, the blade 306 is placed in the retracted (distalmost) position so that it is concealed by the cover 310. The jaws 302, 304 are then opened using the control wires. Biological tissue which is to be cut is then placed between the jaws 302, 304, and the jaws are closed so that the biological tissue is gripped between them. Then, using the microwave emitter structure 312, microwave EM energy is applied to the biological tissue in order to cauterise the biological tissue. Following this, the blade 306 may be pulled along the slot 308 towards the axle 305 in order to cut the biological tissue held between the jaws 302, 304. As the biological tissue was cauterised prior to its being cut, bleeding may be avoided.

Figure 4A:
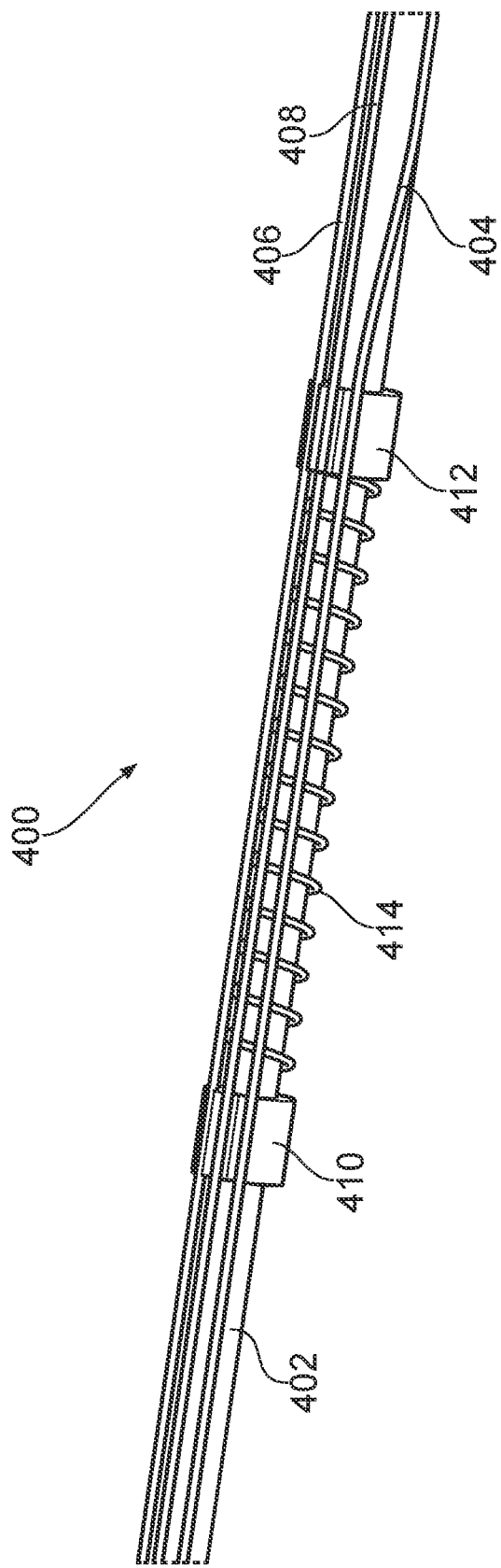
FIGS. 4a-4c are schematic diagrams illustrating a safety mechanism that can be used to actuate a sliding blade of the instrument tip of FIGS. 3a and 3b.
Figure 4B:
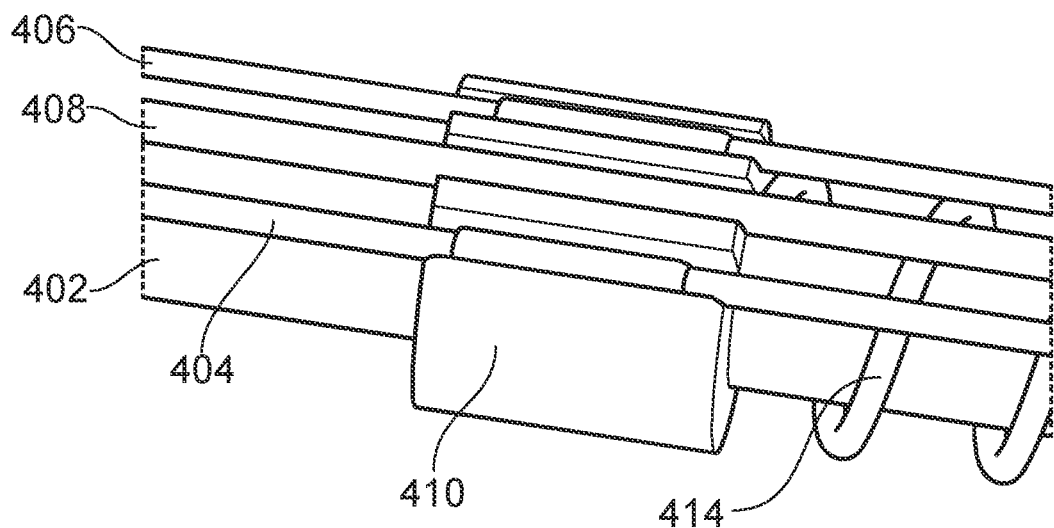
Figure 4C:
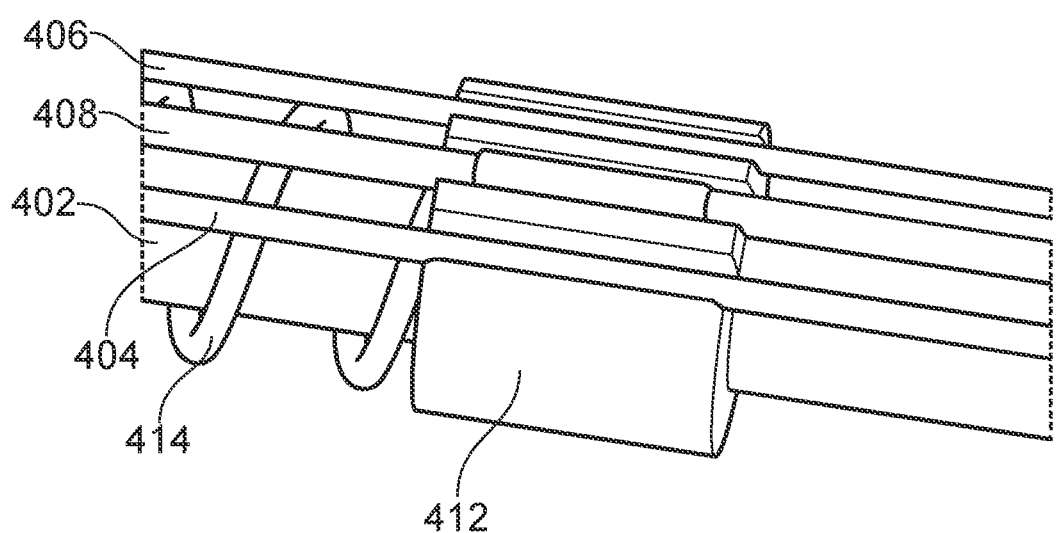

FIGS. 4a, 4b and 4c are schematic diagrams illustrating a safety mechanism 400 that may be used for moving blade 306 along slot 308 in instrument tip 300. The mechanism 400 ensures that there is always a push force applied to the blade 306, such that it is biased towards the retracted position, where it is concealed by the cover 310. The safety mechanism 400 may be located inside the instrument shaft, near a distal end of the instrument shaft where the instrument tip is connected. For illustration purposes, the instrument shaft is not depicted in FIGS. 4a, 4b and 4c.

FIGS. 4a, 4b and 4c show the coaxial transmission line 402 of the electrosurgical instrument, for conveying microwave EM energy to the instrument tip. Also shown are first and second control wires 404 and 406 for opening and closing the jaws of the instrument tip, as discussed above. A third control wire 408 runs through the instrument shaft for moving the blade 306 backwards and forwards along slot 308. Moving third control wire 408 longitudinally along the instrument shaft causes the blade 306 to move along the slot 308. The safety mechanism 400 includes a proximal ring 410 and a distal ring 412 spaced by a helical spring 414. The coaxial transmission line 402 passes through the proximal and distal rings 410, 412 and the helical spring 414. The distal ring 412 is located closer to the instrument tip than the proximal ring 410. Both the proximal and distal rings 410, 412 have three grooves: one for receiving the first control wire 404, one for receiving the second control wire 406 and one for receiving the third control wire 408. FIGS. 4b and 4c show magnified views of the proximal and distal rings 410, 412, respectively.

The first and second control wires 404, 406 are secured to the proximal ring 410 such that they are fixed relative to the proximal ring 410 (i.e. they are not slidable in their respective grooves relative to the proximal ring). For example, the first and second control wires 404, 406 may be glued or soldered to the proximal ring 410. However, the first and second control wires 404, 406 are not fixed relative to the distal ring 412, such that they are slidable in their grooves relative to the distal ring 412. Conversely, the third control wire 408 is not fixed relative to the proximal ring 410, such that it is slidable in its groove relative to the proximal ring 410. The third control wire 408 is however fixed relative to the distal ring 412, such that it is not slidable in its groove relative to the distal ring. The proximal and distal rings 410, 412 are not fixed relative to the coaxial transmission line 402, and can slide relative to the coaxial transmission line 402.

The safety mechanism 400 may be arranged such that the spring 414 provides a biasing force that urges the proximal ring 410 and the distal ring 412 apart. The longitudinal travel of the proximal ring 410 in the proximal direction is limited by the jaws. When the jaws are closed, the proximal ring 410 cannot travel further back along the shaft because is it fixed to the first and second control wires 404, 406. With no external force on the third control wire 408, the separation of the proximal ring 410 and the distal ring 412 determined by the spring may be such that the blade is still retained in the cover when the proximal ring 410 is in this position. The blade can then be moved by applying a force to the third control wire 408 that compresses the spring to permit the distal ring 412 to move closer to the proximal ring 410.

Similarly, the longitudinal travel of the distal ring 412 in the distal direction may be limited by the cover, which present a physical block to distal movement of the blade. When the blade is retained in the cover, the distal ring 412 cannot travel further forward along the shaft because is it fixed to the third control wire 408. The jaws may still be opened in this scenario by applying a force to the first and second control wires 404, 406 that compresses the spring to permit the proximal ring 410 to move closer to the distal ring 412.

It should be noted that alternative safety mechanisms for biasing the position of the blade and/or the jaws may be used. For example, in the case of a safety mechanism which only biases the position of the blade 306, the proximal ring 410 may be fixed relative to the coaxial transmission line 402, and the first and second control wires 404, 406 may be slidable relative to the proximal ring 410. The distal ring 412 may be configured as described above for safety mechanism 400. Then, the compression of the spring 414 acts as described above to bias the blade 306 towards the retracted position, but does exert any force on the first and second control wires 404, 406 to bias the position of the jaws 302, 304.

Figure 5:
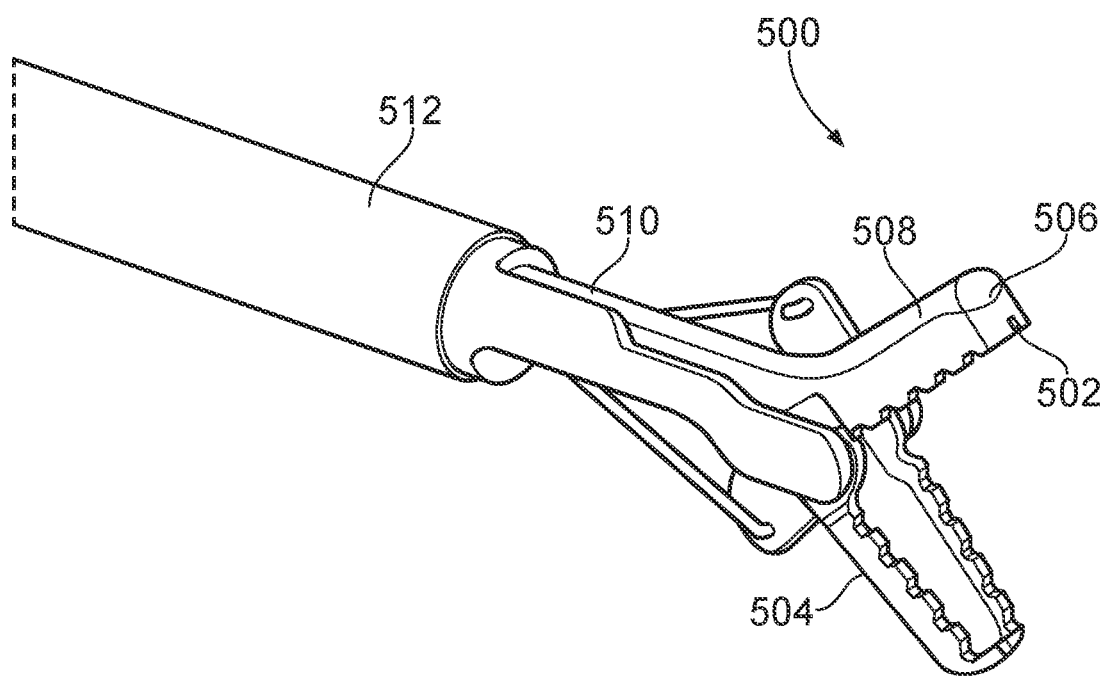
FIG. 5 shows a perspective view of an instrument tip of an electrosurgical forceps instrument that is another embodiment of the invention.

The instrument tip of the electrosurgical instrument of the invention may be configured to perform functions in addition to vessel sealing. For example, the instrument tip may have an auxiliary radiofrequency (RF) dissector element mounted on a distal tip thereon. FIG. 5 shows an example of an instrument tip 500 according to the invention, having a pair of jaws 502, 504 and an RF dissector element 506 mounted on a distal end of jaw 502. The RF dissector element 506 is a bipolar structure that comprises an active electrode mounted in a ceramic tube 508, and a return electrode, which may be fabricated on or integrated with the jaw 502 in the vicinity of the ceramic tube 508. A groove is provided on an upper surface of the jaw 502 to receive the ceramic tube 508. The dissector element 506 is connected to an RF transmission wire 510 which runs through the instrument shaft 512, and which is arranged to convey RF EM energy from an RF EM energy generator located at a proximal end of the electrosurgical instrument. For example, the RF transmission wire 510 may be a copper wire contained in a PTFE jacket.

The RF dissector element 506 can be used for fine bloodless tissue cutting and tissue dissection. In the arrangement shown in FIG. 5, the RF dissector element 506 presents a leading edge that sits proud of the distal end of the jaw 502. This position can enable both side and end-on dissection to be performed. In dry field treatment scenarios (i.e. in the absence of saline or other electrically conductive fluid) it is desirable for the return electrode to be in close proximity to the active electrode that is on the RF dissector element 506. The ratio of the exposed tissue contacting electrode areas is also important to ensure that current flow occurs in a desired manner that causes maximum current density to occur on the leading edge of the RF dissector element 506.

Although the RF dissector element 506 is shown at the distal end of the jaw 502 in FIG. 5, it can be mounted in a variety of orientations or locations on the distal end assembly, e.g. vertically, horizontally, at an angle, on one side, and on either jaw.

Handpiece Structure

Figure 6A:
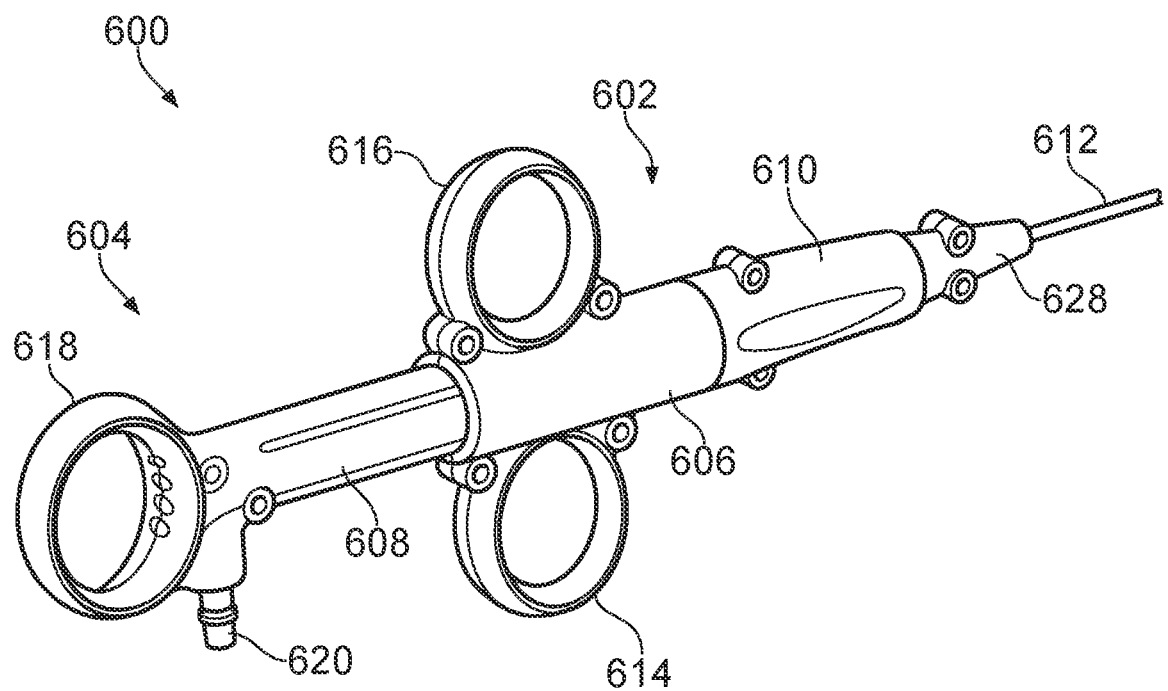
FIG. 6a shows a perspective view of a handpiece of an electrosurgical apparatus that is an embodiment of the invention.

FIG. 6a is an illustration of a handpiece 600 which may be used as part of an electrosurgical apparatus that is an embodiment of the invention. The handpiece 600 includes a body 602 and an actuating portion 604. The body 602 includes a hollow barrel 606 in which a shaft 608 of the actuating portion 604 is slidably engaged. The body 602 also includes a rotator 610 which is rotatably connected to the barrel 606.

The actuating portion 604 is connected to an internal shaft 628 which extends through the barrel 606 and rotator 610, and which protrudes from a distal end of the rotator 610. The internal shaft 628 moves longitudinally with the shaft 608, but is rotatable relative to it. An instrument shaft 612 exits the handpiece 600 from a distal end of the internal shaft 628. For example, the instrument shaft 612 may be instrument shaft 210 described above, which is connected to an instrument tip at its distal end. The instrument shaft 612 is connected to rotate with the internal shaft 628.

The actuating portion 604 is slidable in a longitudinal direction relative to the body 602 along its shaft 608 between two positions: a closed position where a length of the shaft 608 is contained within the barrel 606, and an open position where the length of the shaft 608 is outside the barrel 606. FIG. 6a shows the handpiece 600 with the actuating portion 604 in the open position. The total range of motion of the actuating portion 604 relative to the body 602 may be approximately 35 mm. The longitudinal direction of motion of the actuating portion 604 relative to the body 602 is aligned with a longitudinal axis of the instrument shaft 612 as is passes out of the internal shaft 628. The shaft 608 may include one or more grooves 614 which engage with protrusions (not shown) inside the barrel 606, in order to prevent the actuating portion 604 from rotating relative to the body 602. The body 602 includes a pair of finger rings 614, 616 and the actuating portion 604 includes a thumb ring 618, which may be used to facilitate a user's grip when moving the actuating portion 604 relative to the body 602. The actuating portion further includes an input connector 620 for connecting an interface cable (e.g. interface cable 104) which connects the handpiece 600 to a generator (e.g. generator 102). The input connector 620 may for example be a QMA connector or any other suitable connector for interfacing with the generator.

Figure 6B:
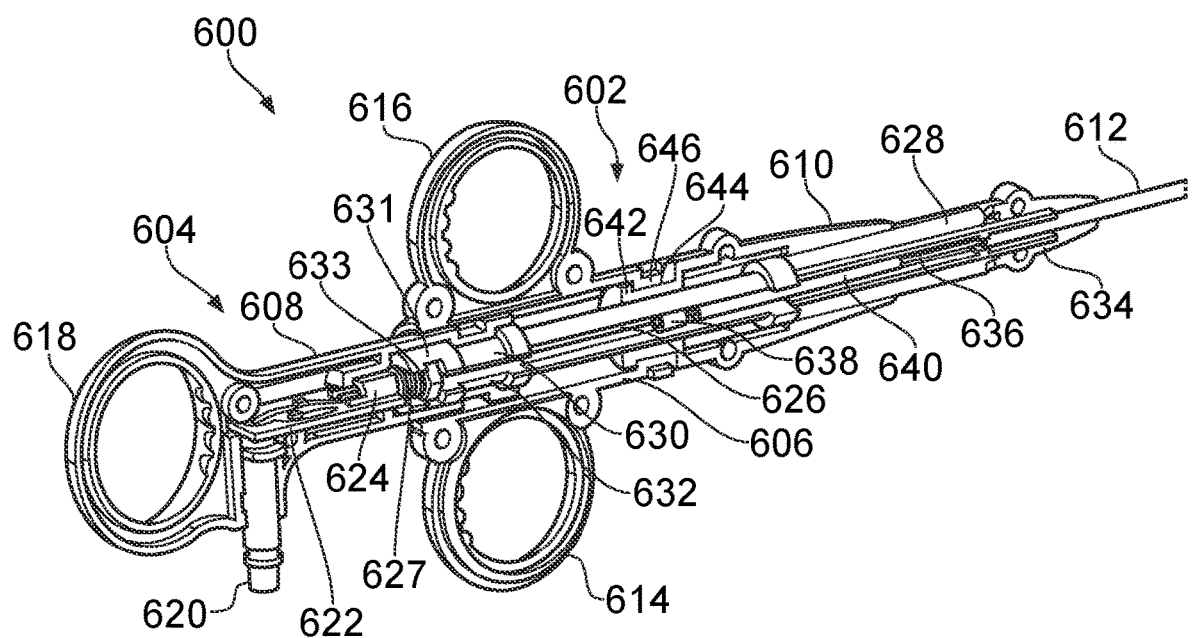
FIG. 6b shows a part cutaway view of the handpiece of FIG. 6a, revealing parts of the internal structure of the handpiece.
Figure 6C:
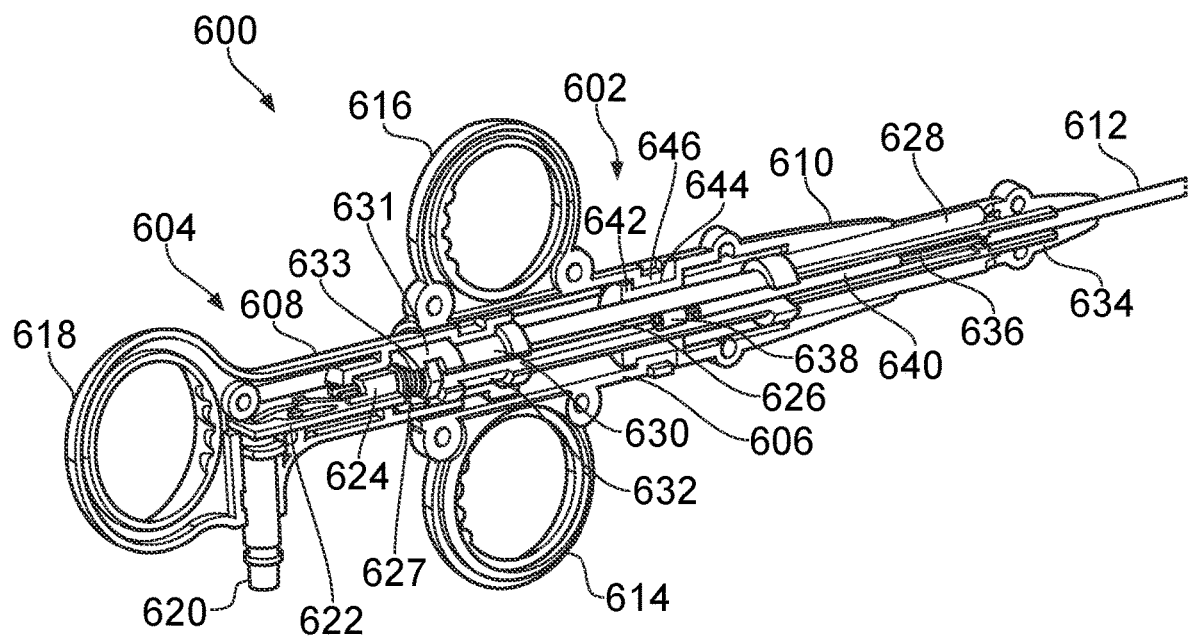

FIG. 6b is a cut-away illustration of the handpiece 600, where certain parts are not shown in order to reveal the internal structure of the handpiece. Where features have already been described above in reference to FIG. 6a, identical reference numerals have been used.

The input connector 620 is electrically connected to a circuit board 622 contained within the shaft 608 of the actuating portion 604. The input connector 620 forms a substantially right angle with the circuit board 622, such that it is oriented along a direction which is substantially perpendicular to the direction of relative motion between the actuating portion and the body 602. In this manner, a cable which is connected to the input connector 620 may not get in a user's way. An output connector 624 is attached at an edge of the circuit board 622. The circuit board 622 contains a circuit which is configured to block RF EM energy input into the input connector 620, and transmit any microwave EM energy input into the connector 620 to the output connector 624. The output connector 624 is electrically connected to a coaxial transmission line 626 via a mating connector 627 on the coaxial transmission line 626. The coaxial transmission line 626 runs through the handpiece 600 and enters the instrument shaft 612 at the distal end of the handpiece 600. The coaxial transmission line 626 may for example correspond to coaxial line 226 described above, which serves to convey microwave EM energy to the instrument tip. The circuit board 622 therefore provides a safety mechanism which prevents RF EM energy from unintentionally being conveyed to the coaxial transmission line 626. The circuit board 622 is described in more detail below.

The electrical connection between the output connector 624 and the coaxial transmission line 626 is rotatable, i.e. it allows the coaxial transmission line to rotate about its axis relative to the output connector 624. Suitable connectors which enable rotatable electrical connections include QMA connectors, micro coaxial (MCX) connectors and microminiature coaxial (MMCX) connectors.

As shown in FIG. 6b, the internal shaft 628 extends through and is longitudinally slidable relative to both the barrel 606 and the rotator 610 of the body 602. A distal end of the internal shaft 628 protrudes from the rotator 610. The length of the protruding portion depends on the position of the shaft 608 of the actuating portion 604. The internal shaft 628 is connected at a proximal end to the shaft 608 of the actuating portion 604, by means of a circumferential recess 630 around an outer surface of the internal shaft 628 which is engaged by a radial protrusion 632 on an inner surface of the shaft 608. The connection between the shaft 608 and the internal shaft 628 prevents the internal shaft 628 from moving longitudinally relative to the shaft 608, but allows the internal shaft 628 to rotate about its axis relative to the shaft 608. The internal shaft 628 may therefore be moved longitudinally backwards and forwards relative to the body 602 by moving the actuating portion 604 relative to the body 602.

The internal shaft 628 may include a proximal portion 631 having a cavity for holding the connector 627 of the coaxial transmission line 626 in position to ensure that it remains securely connected to the output connector 624 on the circuit board 622. Additionally, the connector 627 on the coaxial transmission line 626 may include a protrusion 633 which is configured to engage a slot in the proximal portion 630 of the internal shaft 628, to prevent the connector 627 from moving relative to the internal shaft 628. For example, the protrusion 633 may be a nut which is part of or attached (e.g. by soldering) to the connector 627. The protrusion 627 may also be configured to rotationally lock the connector 627 to the internal shaft 628, such that rotation of the internal shaft 628 causes the connector 627 to rotate.

The coaxial transmission line 626 passes through the internal shaft 628 where, at a distal end thereof, it enters the instrument shaft 612. A length of the instrument shaft 612 is contained within a distal portion 634 of the internal shaft 628, where it is fixed to the internal shaft 628. In this manner, both longitudinal and rotational motion of the internal shaft 628 may be transmitted to the instrument shaft 612. For example, the instrument shaft 612 may be glued using epoxy to the distal portion 634 of the internal shaft 628. Adhesion between the instrument shaft 612 and the internal shaft 628 may be improved by roughing the surface of the instrument shaft 612 before applying the epoxy. In some cases, the length of instrument shaft 612 contained in the distal portion 634 may be approximately 22 mm, to ensure good adhesion.

The rotator 610 is connected to the barrel 606 such that it is rotatable relative to the barrel about a longitudinal axis of the handpiece 600. In the example shown, the rotator 610 has a proximal portion 642 with a circumferential recessed channel 644 that receives a radially inwardly extending protrusion 646 on the barrel 606.

The internal shaft 628 passes through the rotator 610 and is engaged with the rotator 610 such that it is slidable relative to the rotator 610 along its length, but it is not rotatable relative to the rotator 610 (i.e. the rotator 610 and internal shaft 628 are rotationally locked relative to one another). This may be achieved by any kind of interengagement that transfers rotational movement. For example there may be one or more longitudinally oriented cooperating engagement elements (e.g. grooves and teeth) formed on an outer surface of the internal shaft 628 and an inner surface of the rotator 610. The engagement elements may respectively engage with each other to cause the internal shaft 628 to rotate as the rotator 610 is turned on the barrel 606. This in turn causes the instrument shaft 612, which is fixed to the internal shaft 628, to rotate such that an instrument tip connected at a distal end of the instrument shaft 612 may also be caused to rotate. However, as the internal shaft 628 is not rotationally coupled to the actuating portion 604, the actuating portion 604 is not caused to rotate by rotation of the rotator 610. The axis of rotation of the rotator 610 relative to the barrel 606 may be aligned with a longitudinal axis of the internal shaft 628, such that rotation of the rotator 610 causes rotation of the internal shaft 628 about its longitudinal axis.

A length of a main control wire 636 is contained within the internal shaft 628, and exits the handpiece through the instrument shaft 612. The main control wire 636 may be used to open and close jaws on an instrument tip connected at a distal end of the instrument shaft 612. For example, main control wire 636 may correspond to main control wire 242 described above. A proximal end of the main control wire 636 is held fixed relative to the body 602 of the handpiece 600. Therefore, motion of the body 602 relative to the actuating portion 604 may cause the main control wire 636 to move longitudinally along the instrument shaft 612. This is because the longitudinal position of the instrument shaft 612 is held fixed relative to the actuating portion 604 (by means of the internal shaft 628, which is connected at one end to the actuating portion 604 and at another end to the instrument shaft 612), whilst the main control wire 636 is movable with the body 602 relative to the actuating portion 604, and thus the instrument shaft 612.

Thus, a user may move the actuating portion 604 relative to the body 602 in order to move the main control wire 636 backwards and forwards relative to the instrument shaft 612 and control the opening and closing of jaws on an instrument tip connected at a distal end of the instrument shaft 612.

There are several possible ways for holding the proximal end of the main control wire 636 fixed relative to the body 602 of the handpiece 600. In the example shown, a block 638 is attached to the proximal end of the main control wire 636. The block 638 may for example be a piece of metal which is soldered or welded to the proximal end of the main control wire 638. The block 638 may be configured to fit in a holder (not shown) which is rigidly connected to the rotator 610, such that longitudinal motion of the body 602 relative to the actuating portion 604 is transmitted to the block 638 (and hence the main control wire 636) via the holder. The holder may be connected to the rotator 610 through an opening in a side wall of the internal shaft 628.

A portion of the main control wire 636 in the internal shaft 628 may be contained in a protective tube 640. The protective tube may be made of any suitable material (e.g. PTFE), and may serve to prevent the main control wire 636 from bending when the handpiece 600 is opened. Alternatively, a metal tube may be soldered or welded to the main control wire 636 to achieve the same effect.

The relative linear motion between the actuating portion 604 and the body 602 directly controls linear motion of the main control wire 636 relative to the instrument shaft 612. This may enable a user to accurately control the opening and closing of jaws on an instrument tip at the distal end of the instrument shaft 612. Furthermore, the configuration of the handpiece 600 enables a user to comfortably hold the handpiece 600 in one hand and control the opening and closing of the jaws with one hand (by placing fingers of one hand in the finger rings 614, 616, 618). The user may also simultaneously rotate the rotator 610 with the other hand, in order to rotate the instrument tip. The orientation of the input connector 620 may ensure that any cable connected to the input connector 620 does not interfere with a user's operation of the handpiece 600. In this manner, the user isn't forced to hold the handpiece 600 in an awkward position in order to accommodate a cable, which might cause stress on the user's wrist.

RF Blocking Circuit Board

Figure 7A:
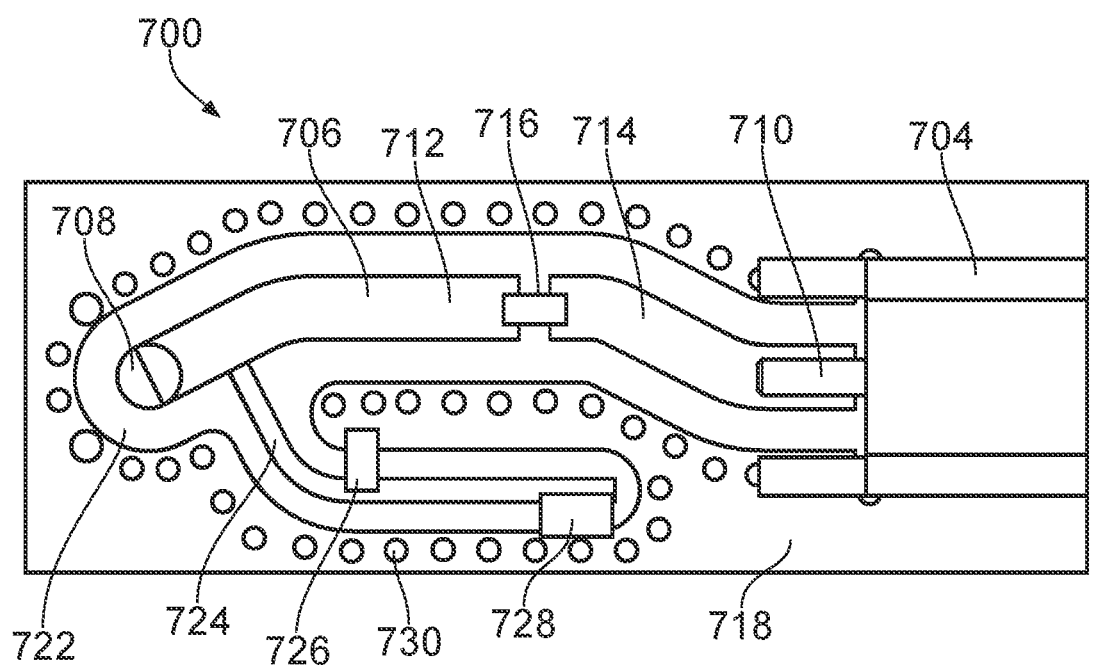
FIG. 7a is a top view of a circuit board that can be mounted within a handpiece of an electrosurgical apparatus that is an embodiment of the invention.
Figure 7B:
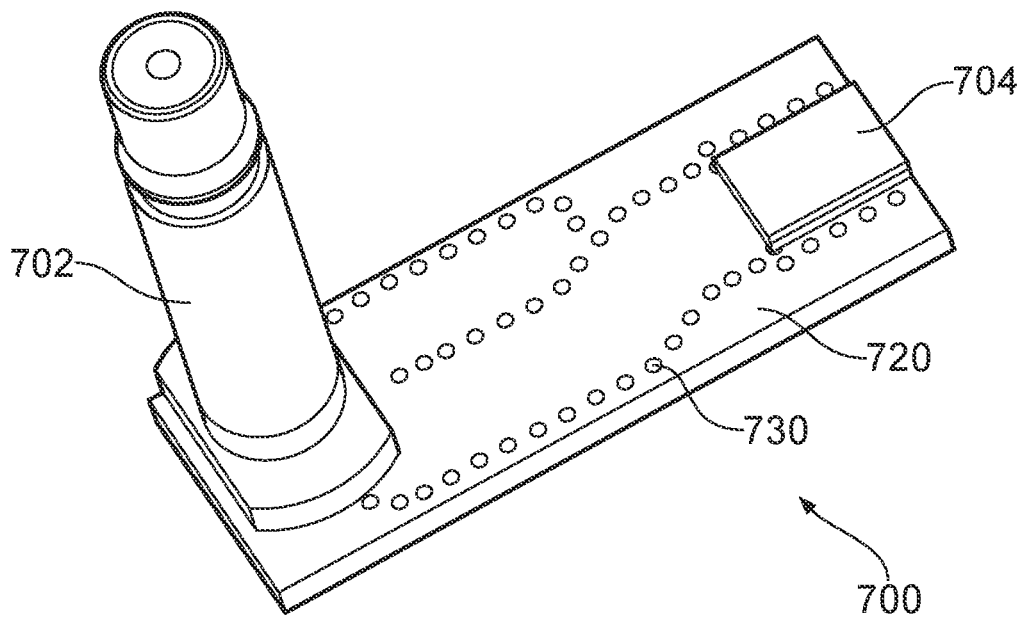
Figure 7C:
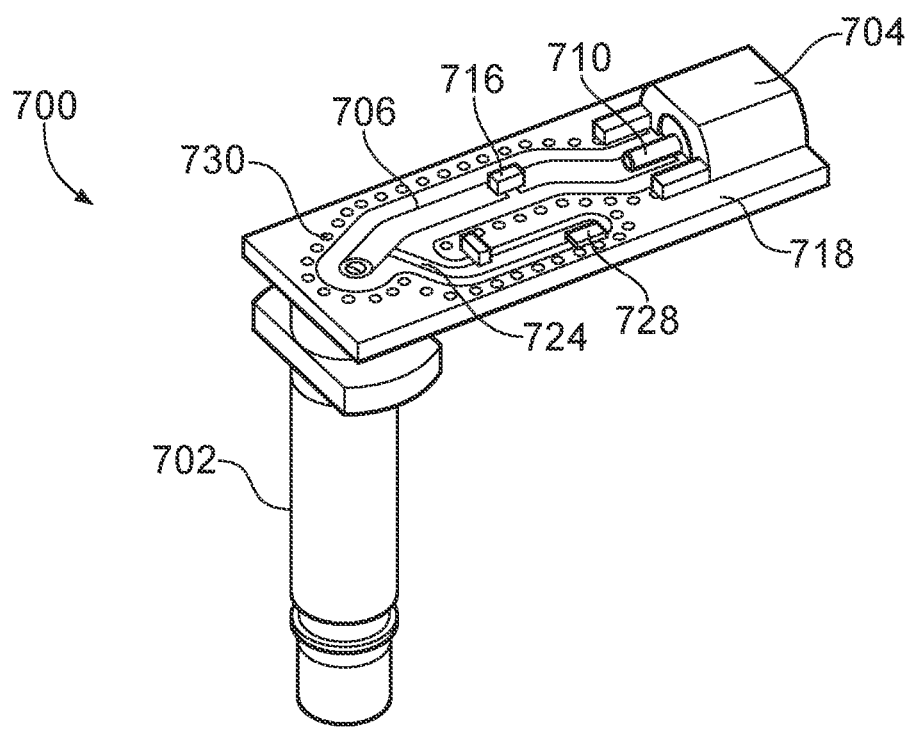

FIG. 7a shows a schematic diagram of a top view of an upper surface of the circuit board 700 which may be contained in a handpiece of an electrosurgical instrument that is an embodiment of the invention. For example, circuit board 700 may correspond to circuit board 622 discussed above in relation to handpiece 600. FIG. 7*b* shows a perspective view of a lower surface of the circuit board 700, whilst FIG. 7*c* shows perspective view of a upper surface of the circuit board 700.

The circuit board 700 includes an input connector 702 mounted on its lower surface, and an output connector 704 mounted near an edge of the circuit board 700. The circuit board 700 contains a RF blocking circuit on its upper surface which is configured to transmit microwave EM energy from the input connector 702 to the output connector 704, whilst blocking any RF EM energy from being transmitted from the input connector 702 to the output connector 704.

As shown in FIG. 7*a*, the RF blocking circuit on the circuit board 700 includes a main strip line 706. An inner (active) conductor of the input connector 704 is electrically connected to the main strip line 706 at a connection point 708. A hole through the circuit board 700 may be provided so that the inner conductor of the input connector 704 can be electrically connected to the main strip line 706. The main strip line 706 is connected at a distal end to an inner conductor 710 of the output connector 704. There is a break in the main strip line 706, dividing the main strip line 706 into a first portion 712 and a second portion 714. The first and second portions 712, 714 of the main strip line 706 are connected by an RF blocking capacitor 716, which is arranged to block RF EM energy from being transmitted along the main strip line 706 to the output connector 704. For example, the RF blocking capacitor 716 may have a capacitance of approximately 3.3 pF.

The upper and lower surfaces of the circuit board 700 each include a respective ground plane 718 and 720. Ground planes 718 and 720 may for example be layers of metal which cover most of the upper and lower surfaces respectively. The main strip line 706 is isolated from the ground plane 718 by an isolating barrier 722 which surrounds the main strip line 706. The ground plane 720 on the lower surface is electrically connected to an outer shell of the input connector 702. The output connector 704 is mounted on the circuit board 700 such that an outer shell of the output connector 704 is electrically connected to both ground planes 718 and 720. The outer shell of the input connector 702 may be configured to be connected to a ground of a generator (e.g. generator 102 via interface cable 104). In this manner, the ground planes 718, 720 and the outer shell of the output connector 704 may be grounded through a generator connected to the input connector 702.

The RF blocking circuit on the upper surface may further include a stub 724 which branches off from the main strip line 706 before the RF blocking capacitor 716. A microwave shorting capacitor 726 may be located on the stub 724 approximately one quarter-wavelength (with respect to the wavelength of microwave EM energy used) away from the main strip line 706. The microwave shorting capacitor 726 is connected between the stub 724 and the ground plane 718, and acts as a short to ground for microwave EM energy. In this manner, the stub appears like a microwave open circuit at the main strip line 706. The microwave shorting capacitor 726 may have a similar capacitance to the RF blocking capacitor 716. After the microwave shorting capacitor 726 there is a load resistor 728 connected between the stub 724 and the ground plane 718. Any RF EM energy fed into the RF blocking circuit must pass into the load resistor 728 where it may be dissipated, as RF EM energy is blocked from passing along the main strip line 706 by the RF blocking capacitor 716. The resistance of the load resistor 728 may be selected such that it causes a generator connected to the circuit board 700 to produce an error signal if RF EM energy is accidentally fed into the RF blocking circuit. The load resistor 728 may for example have a resistance of approximately 9.1 Ohms.

The capacitance values of RF blocking capacitor 716 and microwave shorting capacitor 726 may be selected such that they provide a reasonably low impedance at microwave frequencies (e.g. 5.8 GHz), and a reasonably high impedance at RF frequencies (e.g. 400 kHz). In other words, capacitors 716 and 726 should appear close to a short at microwave frequencies, and close to an open circuit at RF frequencies. The RF blocking circuit may thus provide a good match for the microwave energy into the output 704. The circuit board 700 may be made from any suitable circuit board material. For example the circuit board may be made from RO3006 laminate from Rogers Corporation. This material has a dielectric constant of around 6, allowing the design of the circuit board 700 to be miniaturised.

The circuit board 700 may further include a series of vias 730 placed along the main strip line 706 and stub 724, in order to reduce interference caused by stray radiation. The vias 730 may be through-holes in the circuit board. In order to further reduce stray radiation, a shielding enclosure (e.g. made of metal) may be placed over the upper surface of the circuit board 700. The circuit board 700 may also be completely enclosed in a shielding enclosure. Where the circuit board 700 is contained in a handpiece (e.g. handpiece 600), it may be possible to shield the circuit board 700 by applying a metal coating to an internal surface of the handpiece, such that the circuit board 700 is partially or totally surrounded by the metal coating when it is mounted in the handpiece.

The circuit board 700 serves as an added safety mechanism to ensure that RF EM energy is not accidentally fed into the electrosurgical instrument. The circuit board 700 and prevents RF EM energy from being transmitted from a generator to an instrument tip, where unwanted RF EM energy could cause damage to a patient. As the circuit board is directly integrated with the handpiece of the electrosurgical instrument, it is effective even in situations where the user is misusing the electrosurgical instrument (e.g. when the user has connected the wrong generator to the handpiece). It should be noted that circuit board 700 is shown by way of example only, and circuit boards having alternative configurations may also be used to achieve the same effect.

Figure 8A:
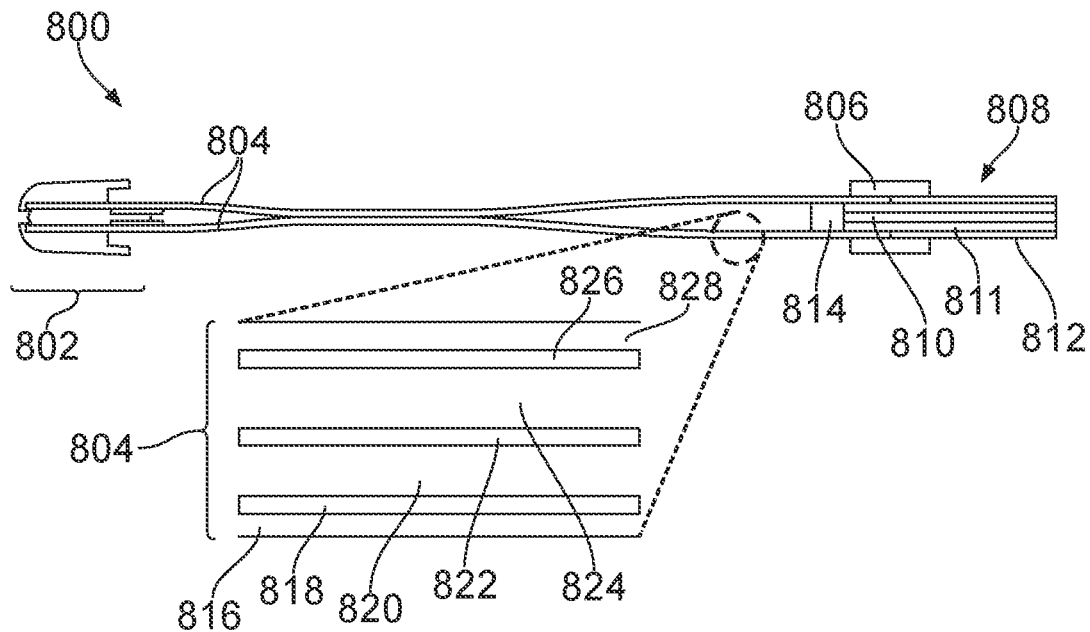
FIG. 8A is a schematic side view of an energy delivery structure that can be used in an electrosurgical forceps instrument that is an embodiment the invention, and includes an inset showing a magnified cross-sectional view through an electrode strip of the energy delivery structure.

FIG. 8A is a schematic side view of one example of an energy delivery structure 800 that can be used in an electrosurgical forceps instrument of the type set out above, where both jaws 802 are arranged to deliver energy into tissue gripped therebetween. Each jaw receives energy from a coaxial cable 808 via a respective flexible electrode strip 804 that can extend through the distal bracket (not shown) in the manner described above.

In this example, the flexible electrode strip 804 conveys energy in a longitudinal direction using a stripline-type transmission line structure, a cross-section of which is shown in the magnified image inset in FIG. 8A. The stripline comprises a flexible planar structure comprising a centre conductor layer 822 separated from a pair of ground plane layers 818, 826 of opposing sides thereof by a pair of flexible dielectric layers 820, 824. The ground plane layers are covered on their outermost surfaces (i.e. the surfaces facing away from the centre conductor layer 822) by respective dielectric (insulating) cover layers 816, 828.

A proximal end of each flexible electrode strip 804 is connected to a distal end of the coaxial cable 808 at a connector 806. The connector 806 may be a sleeve or tube that lies over a region of overlap between the flexible electrode strips 804 and the coaxial cable 808. The coaxial cable 808 comprises an inner conductor 810 separated from an outer conductor 812 by a dielectric material 811.

The inner conductor 810 and dielectric material 811 protrude beyond a distal end of the outer conductor 812. The inner conductor 810 is electrically connected to a conductive contact block 814 which in turn is electrically connector to an exposed portion of a centre conductor 822 within each flexible electrode strip 804. The centre conductor may be exposed by cutting away, etching or otherwise removing a section of the first cover layer 816, lower ground plane layer 818 and first flexible dielectric layer 820 in the region of contact with the conductive contact block 814.

Meanwhile the outer conductor 812 is electrically connected to one of the ground plane layers, e.g. by exposing a distal portion of an upper ground layer 826 and bringing it into electrical contact with the outer conductor 812, e.g. via a conductive layer on the inner surface of the connector 806. The ground plane layers 818, 826 may be electrically connected to each other by one or more vias (not shown) filled with conductive material that extend through the flexible dielectric layers 820, 824 in side regions of the stripline where the centre conductor does not exist. For example, the width of the centre conductor layer 822 may be less than the width of the ground plane layers 820, 824 along the length of the stripline. This means that the ground plane layers 820, 824 extend width-wise beyond a side edge on the centre conductor layer on one or both sides thereof. The vias may be formed between the ground plane layers 820, 824 in this side zone.

At a distal end of the stripline, the centre conductor layer 822 and one or both of the ground plane layers may be exposed to form the electrodes discussed above.

Figure 8B:
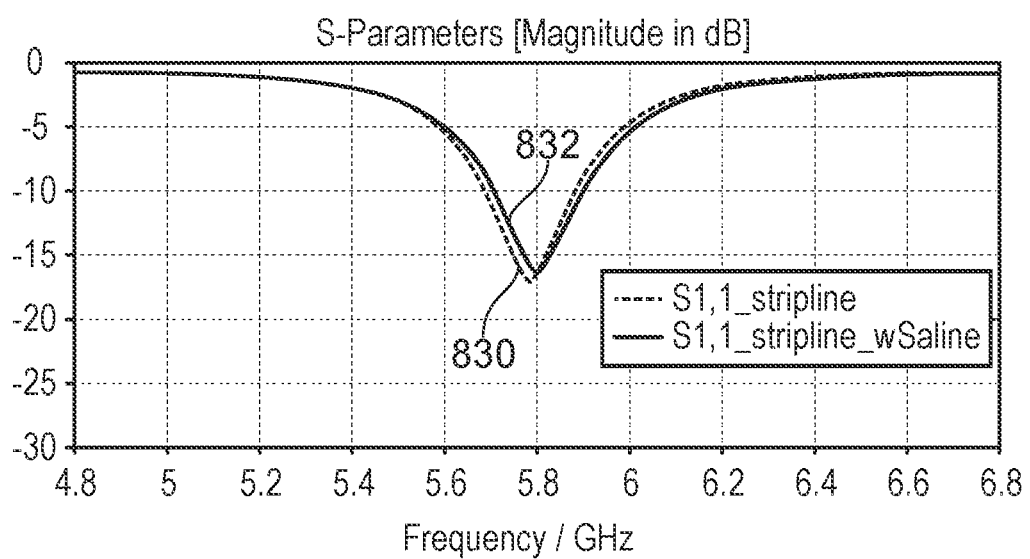
FIG. 8B is a graph showing return loss for the energy delivery structure of FIG. 8A when in tissue and when immersed in saline.

Using a stripline in the electrode strips provides a more isolated energy delivery structure than the microstrip arrangement discussed above. With a stripline, the energy is almost completely contained between the two ground plane layers 820, 824 so that no signals are exposed to the external surfaces. An advantage of this arrangement is that the presence of saline or other conductive fluid around the distal tip of the instrument does not adversely affect energy delivery. This advantage is demonstrated by the graph shown in FIG. 8B, where the line 830 indicating return loss in the presence of saline is very similar to the line 832 indicating return loss in tissue. This is further supported by the power absorption breakdown in each scenario:

TABLE 1

Power absorption with and without presence of saline

| Model | Power absorbed in tissue | Power absorbed in saline |
|---|---|---|
| Saline not present | 66.0% | — |
| Saline present | 61.8% | 0.56% |

Figure 9A:
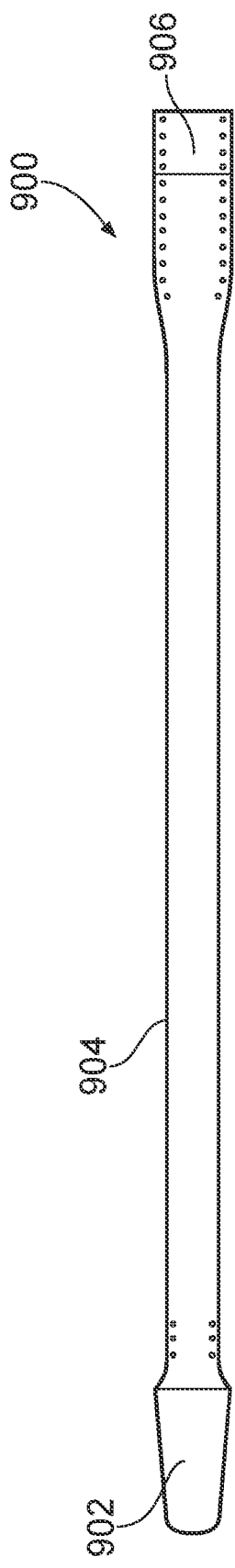
FIGS. 9A and 9B show top and bottom views of an example electrode strip suitable for use in the energy delivery structure of FIG. 8A.
Figure 9B:
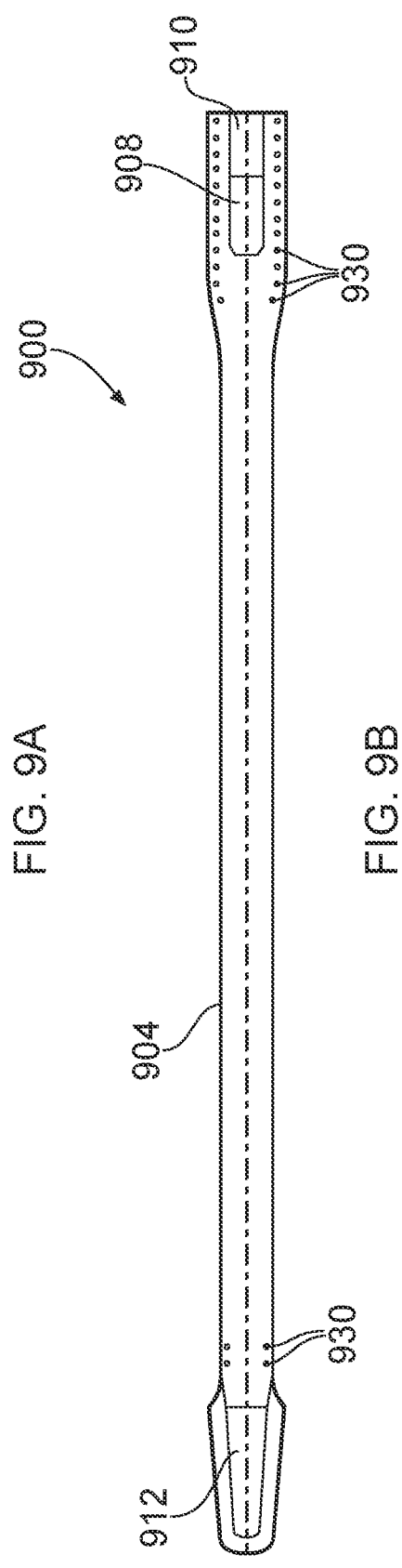

FIGS. 9A and 9B show top and bottom views of an example electrode strip 900 suitable for use in the energy delivery structure of FIG. 8A. The electrode strip 900 comprises an elongate planar stripline 904 having shaped distal and proximal ends where it connects to a respective jaw and coaxial cable respectively.

Figure 9C:
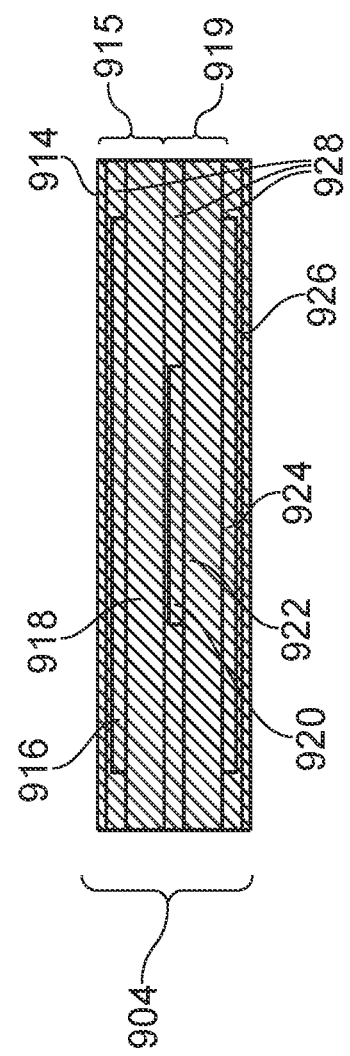
FIG. 9C is a magnified cross-sectional view through a stripline-type transmission line used in the electrode strip of FIGS. 9A and 9B.

FIG. 9C is a magnified cross-sectional view through the stripline 904. The transmission line structure itself is formed from a pair of flexible laminated dielectric substrates 915, 916. Each laminated dielectric substrate comprises a flexible dielectric (e.g. polyimide) layer having a conductive material, e.g. copper, laminated on one or both surfaces thereof. The laminated conductive material can be given a desired shape on the substrate by etching or the like.

In this example, an upper laminated substrate 915 comprises a first dielectric layer 918 and an upper ground plane layer 916. A lower laminated substrate 919 comprises a second dielectric layer 922, a centre conductor layer 920, and a lower ground plane layer 924. The upper laminated substrate 915 and the lower laminated structure are mounted together, e.g. using a (non-conductive) adhesive 928, so that the centre conductor layer 920 is sandwiched between the first and second dielectric layers 918, 922. The centre conductor layer 920 has a smaller width than the upper and lower ground plane layers 916, 924 to for a stripline. The upper laminated substrate 915 may be a single-sided laminate, or may be formed from a double-sided laminate by completely etching away one of the conductive surfaces.

The transmission line is sandwiched between a pair of outer cover layers 914, 926, made of flexible insulating material, such as polyimide. The cover layer 914, 926 may be adhered to the adjacent surface of the stripline. Although not shown in FIG. 9C, the upper and lower ground plane layers 916, 924 are electrically connected by a series of vias 930 formed at proximal and distal ends of the electrode strip in the region spaced in the width direction from the centre conductor layer 920. The vias extend through the first and second dielectric layers 918, 922 between the upper and lower ground plane layers 916, 924 and carry conductive material to make an electrical connection.

The proximal end of the electrode strip is adapted to enable the conductive layers to connect to a coaxial cable. On the top surface of the electrode strip 900 (shown in FIG. 9A) the upper cover layer 914 is removed to expose a portion 906 of the upper ground plane layer 916, which in turn is electrically connected to an outer conductor of the coaxial cable, e.g. in a manner similar to that described above with respect to FIG. 8A. On the bottom surface of the electrode strip 900 (shown in FIG. 9B) the lower cover layer 926, lower ground plane layer 924 and second dielectric layer 922 are removed to expose a portion 908 of the centre conductor layer 920, which in turn is electrically connected to an inner conductor of the coaxial cable, e.g. in a manner similar to that described above with respect to FIG. 8A. In practice, a channel 910 is removed from the three layers mentioned above in order to receive a length of the inner conductor that protrudes from a distal end of the coaxial cable. The centre conductor layer 920 does not extend to a proximal end of the electrode strip 900 to reduce or minimise energy loss at this junction.

The distal end of the electrode strip 900 is adapted to provide the energy delivery electrode in the respective jaw. On the top surface of the electrode strip 900 (shown in FIG. 9A) the upper cover layer 914 terminates before the distal end to expose a portion 902 of the upper ground plane layer 916, which in turn is electrically connected to its respective jaw. On the bottom surface of the electrode strip 900 (shown in FIG. 9B) the lower cover layer 926, lower ground plane layer 924 and second dielectric layer 922 terminate before the distal end to expose a portion 912 of the centre conductor layer 920, from which energy is delivered. The exposed portion is set back from the edges of first dielectric layer 918 to control the shape of the emitted field.

The invention claimed is:

1. An electrosurgical forceps instrument comprising:
a flexible shaft defining a lumen;
a coaxial cable for conveying microwave energy disposed within the lumen of the flexible shaft;
a rigid bracket mounted at a distal end of the flexible shaft;
a pair of jaws pivotably mounted on the rigid bracket, the pair of jaws being movable relative to each other to open and close a gap between opposing inner surfaces thereof; and
an actuating element disposed within the lumen of the flexible shaft and extending therefrom through the rigid bracket to operably engage the pair of jaws,
wherein the pair of jaws comprises a first jaw having an energy delivery structure attached to an inner surface therefore, the energy delivery structure comprising a flexible dielectric substrate having a first electrode and an second electrode formed thereon,
wherein the energy delivery structure is connected to receive the microwave energy from the coaxial cable,
wherein the first electrode and the second electrode are arranged to emit the microwave energy received by the energy delivery structure into the gap between the pair of jaws; and
wherein the flexible dielectric substrate comprises a proximal portion that passes through the rigid bracket and extends between a distal end of the coaxial cable and a proximal end of the inner surface, wherein the proximal portion is deformable upon opening and closing of the pair of jaws.

2. An electrosurgical forceps instrument according to claim 1, wherein the pair of jaws are pivotably mounted about a common axis.

3. An electrosurgical forceps instrument according to claim 1, wherein the pair of jaws comprises a first jaw and a second jaw, and wherein the actuating element comprises a first control wire connected to the first jaw and a second control wire connected to the second jaw, wherein the first control wire and second control wire are movable in a longitudinal direction relative to the bracket to effect opening and closing, of the pair of jaws.

4. An electrosurgical forceps instrument according to claim 3, wherein the actuating element comprises a main control wire that extends through the lumen of the flexible shaft, wherein the main control wire bifurcates at a distal end thereof to form the first control wire and the second control wire.

5. An electrosurgical forceps instrument according to claim 1 including a retaining frame mounted within a proximal portion of the lumen, the retaining frame having a first mounting region for the coaxial cable and a second mounting region for the actuating element, whereby the retaining frame is arranged the hold the coaxial cable and the actuating element in a fixed orientation relative to each other.

6. An electrosurgical forceps instrument according to claim 5 includes a sleeve formed around the retaining frame, coaxial cable and actuating element within the lumen of the flexible shaft.

7. An electrosurgical forceps instrument according to claim 5, wherein the retaining frame has a distal end spaced longitudinally from the rigid bracket.

8. An electrosurgical forceps instrument according to claim 1, wherein the flexible dielectric substrate has a pair of conductive tracks formed thereon for conveying microwave energy from the coaxial cable to the first electrode and second electrode.

9. An electrosurgical forceps instrument according to claim 8, wherein the pair of conductive tracks comprise a first conductive track electrically connected to an inner conductor of the coaxial cable, and a second conductive track electrically connected to an outer conductor of the coaxial cable.

10. An electrosurgical forceps instrument according to claim 1, wherein the flexible dielectric substrate is a ribbon of insulating material having electrically conductive layer fabricated thereon to provide the first electrode and the second electrode.

11. An electrosurgical forceps instrument according to claim 1, wherein the first jaw has a longitudinal slot formed therein, and wherein the instrument further comprises:
a blade slidably mounted within the longitudinal slot on the first jaw; and
a blade control wire disposed within and extending from the lumen to operably engage the blade.

12. An electrosurgical forceps instrument according to claim 11, wherein the first jaw comprises a cover portion at a distal end thereof, the cover portion being sized to retain the blade in a retracted position.

13. An electrosurgical forceps instrument according to claim 12, wherein the blade is biased into the retracted position.

14. An electrosurgical forceps instrument according to claim 11, wherein the blade control wire is operably coupled to the actuating element such that movement of the blade away from the retracted position urges the pair of jaws towards a closed position.

15. An electrosurgical forceps according to claim 1, wherein the pair of jaws are dimensioned to fit within an instrument channel of a surgical scoping device.

16. A handpiece for controlling an electrosurgical instrument, the handpiece comprising:
a body;
a flexible shaft extending from a distal end of the body;
a coaxial cable extending through a lumen defined by the flexible shaft, the coaxial cable being for connection to an electrosurgical instrument locatable at a distal end of the flexible shaft;
a control rod extending through the lumen, the control rod being for connection to electrosurgical instrument locatable at a distal end of the flexible shaft;
an actuating element slidably mounted on the body; and
a rotator rotatably mounted on the body,
wherein the coaxial cable and the flexible shaft are mounted to slide relative to the body with the actuating element and rotate relative to the body with the rotator, and
wherein the control rod has a proximal portion that is mounted in a longitudinally fixed position relative to the body.

17. A handpiece according to claim 16, wherein the control rod is rotatable with respect to the body.

18. A handpiece according to claims 16 wherein the actuating element comprises a shaft mounted to slide in a longitudinal direction within the body, the longitudinal direction being aligned with a direction in which the flexible shaft extends from the body.

19. A handpiece according to claim 16 including a power input port on the actuating element, the power input port being connected to transfer power received therein to the coaxial cable.

20. A handpiece according to claim 19, wherein a connection direction into the power input port extends perpendicularly to the direction in which the actuating element is slidable relative to the body.

21. A handpiece according to claim 19 having a radiofrequency (RF) blocking circuit mounted in the actuator element between the power input port and the coaxial cable.

22. An electrosurgical apparatus comprising:
- an electrosurgical generator for supplying microwave energy;
- a surgical scoping device having an instrument cord for insertion into a patient's body, the instrument cord having an instrument channel extending therethrough;
- a handpiece according to claim 16 connected to receive the microwave energy from the electrosurgical generator, the flexible shaft of the handpiece passing through the instrument channel of the surgical scoping device; and
- an electrosurgical forceps instrument connected at a distal end of the flexible shaft of the handpiece,
- wherein the actuating element is connected to control opening and closing of the electrosurgical forceps instrument, and
- wherein the rotator is configured to control rotation of the electrosurgical forceps instrument relative to the instrument channel.

\* \* \* \* \*